(12) United States Patent
Wu

(10) Patent No.: US 7,658,880 B2
(45) Date of Patent: Feb. 9, 2010

(54) POLYMERIC STENT POLISHING METHOD AND APPARATUS

(75) Inventor: Patrick P. Wu, Mountain View, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 851 days.

(21) Appl. No.: 11/194,089

(22) Filed: Jul. 29, 2005

(65) Prior Publication Data

US 2007/0023974 A1    Feb. 1, 2007

(51) Int. Cl.
*B29C 71/04*    (2006.01)
(52) U.S. Cl. .................. 264/491; 264/345; 264/162
(58) Field of Classification Search ............ 264/345, 264/162, 491, 405, 476, 492; 623/1.1
See application file for complete search history.

(56) References Cited

U.S. PATENT DOCUMENTS

| | | | |
|---|---|---|---|
| 3,687,135 A | | 8/1972 | Stroganov et al. |
| 3,839,743 A | | 10/1974 | Schwarcz |
| 3,900,632 A | | 8/1975 | Robinson |
| 4,001,110 A | * | 1/1977 | Geen et al. .............. 264/40.1 |
| 4,074,958 A | * | 2/1978 | Molenaar ................ 425/71 |
| 4,104,410 A | | 8/1978 | Malecki |
| 4,110,497 A | | 8/1978 | Hoel |
| 4,321,711 A | | 3/1982 | Mano |
| 4,346,028 A | | 8/1982 | Griffith |
| 4,510,005 A | * | 4/1985 | Nijman ................ 156/221 |
| 4,596,574 A | | 6/1986 | Urist |
| 4,599,085 A | | 7/1986 | Riess et al. |
| 4,612,009 A | | 9/1986 | Drobnik et al. |
| 4,633,873 A | | 1/1987 | Dumican et al. |
| 4,656,083 A | | 4/1987 | Hoffman et al. |
| 4,718,907 A | | 1/1988 | Karwoski et al. |
| 4,722,335 A | | 2/1988 | Vilasi |
| 4,723,549 A | | 2/1988 | Wholey et al. |
| 4,732,152 A | | 3/1988 | Wallstén et al. |
| 4,733,665 A | | 3/1988 | Palmaz |
| 4,739,762 A | | 4/1988 | Palmaz |
| 4,740,207 A | | 4/1988 | Kreamer |

(Continued)

FOREIGN PATENT DOCUMENTS

DE    44 07 079    9/1994

(Continued)

OTHER PUBLICATIONS

U.S. Appl. No. 10/317,435, filed Dec. 11, 2002, Hossainy et al.

(Continued)

*Primary Examiner*—Khanh Nguyen
*Assistant Examiner*—Saeed M Huda
(74) *Attorney, Agent, or Firm*—Squire, Sanders & Dempsey LLP

(57) ABSTRACT

A method and apparatus for simultaneously polishing the inner and outer surfaces of an unpolished polymeric stent using a heat process. The unpolished stent can be mounted, for example, on a "spiral-mandrel," a tubular helical structure with gaps in between a series of coils of the structure. Heat from a heat source can then applied to the spiral-mandrel at a range between the glass transition temperature and melting temperature of the polymer of the stent.

29 Claims, 9 Drawing Sheets

U.S. PATENT DOCUMENTS

| | | |
|---|---|---|
| 4,743,252 A | 5/1988 | Martin, Jr. et al. |
| 4,768,507 A | 9/1988 | Fischell et al. |
| 4,776,337 A | 10/1988 | Palmaz |
| 4,800,882 A | 1/1989 | Gianturco |
| 4,816,339 A | 3/1989 | Tu et al. |
| 4,818,559 A | 4/1989 | Hama et al. |
| 4,850,999 A | 7/1989 | Planck |
| 4,877,030 A | 10/1989 | Beck et al. |
| 4,878,906 A | 11/1989 | Lindemann et al. |
| 4,879,135 A | 11/1989 | Greco et al. |
| 4,886,062 A | 12/1989 | Wiktor |
| 4,902,289 A | 2/1990 | Yannas |
| 4,977,901 A | 12/1990 | Ofstead |
| 4,994,298 A | 2/1991 | Yasuda |
| 5,019,090 A | 5/1991 | Pinchuk |
| 5,028,597 A | 7/1991 | Kodama et al. |
| 5,059,211 A | 10/1991 | Stack et al. |
| 5,062,829 A | 11/1991 | Pryor et al. |
| 5,084,065 A | 1/1992 | Weldon et al. |
| 5,085,629 A | 2/1992 | Goldberg et al. |
| 5,100,429 A | 3/1992 | Sinofsky et al. |
| 5,104,410 A | 4/1992 | Chowdhary |
| 5,108,417 A | 4/1992 | Sawyer |
| 5,108,755 A | 4/1992 | Daniels et al. |
| 5,112,457 A | 5/1992 | Marchant |
| 5,123,917 A | 6/1992 | Lee |
| 5,156,623 A | 10/1992 | Hakamatsuka et al. |
| 5,163,951 A | 11/1992 | Pinchuk et al. |
| 5,163,952 A | 11/1992 | Froix |
| 5,163,958 A | 11/1992 | Pinchuk |
| 5,167,614 A | 12/1992 | Tessmann et al. |
| 5,192,311 A | 3/1993 | King et al. |
| 5,197,977 A | 3/1993 | Hoffman, Jr. et al. |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,306,294 A | 4/1994 | Winston et al. |
| 5,328,471 A | 7/1994 | Slepian |
| 5,330,500 A | 7/1994 | Song |
| 5,342,348 A | 8/1994 | Kaplan |
| 5,342,395 A | 8/1994 | Jarrett et al. |
| 5,342,621 A | 8/1994 | Eury |
| 5,356,433 A | 10/1994 | Rowland et al. |
| 5,383,925 A | 1/1995 | Schmitt |
| 5,385,580 A | 1/1995 | Schmitt |
| 5,389,106 A | 2/1995 | Tower |
| 5,399,666 A | 3/1995 | Ford |
| 5,423,885 A | 6/1995 | Williams |
| 5,441,515 A | 8/1995 | Khosravi et al. |
| 5,443,458 A | 8/1995 | Eury et al. |
| 5,443,500 A | 8/1995 | Sigwart |
| 5,455,040 A | 10/1995 | Marchant |
| 5,464,650 A | 11/1995 | Berg et al. |
| 5,502,158 A | 3/1996 | Sinclair et al. |
| 5,514,379 A | 5/1996 | Weissleder et al. |
| 5,527,337 A | 6/1996 | Stack et al. |
| 5,545,408 A | 8/1996 | Trigg et al. |
| 5,554,120 A | 9/1996 | Chen et al. |
| 5,556,413 A | 9/1996 | Lam |
| 5,578,046 A | 11/1996 | Liu et al. |
| 5,578,073 A | 11/1996 | Haimovich et al. |
| 5,591,199 A | 1/1997 | Porter et al. |
| 5,591,607 A | 1/1997 | Gryaznov et al. |
| 5,593,403 A | 1/1997 | Buscemi |
| 5,593,434 A | 1/1997 | Williams |
| 5,599,301 A | 2/1997 | Jacobs et al. |
| 5,599,922 A | 2/1997 | Gryaznov et al. |
| 5,605,696 A | 2/1997 | Eury et al. |
| 5,607,442 A | 3/1997 | Fischell et al. |
| 5,607,467 A | 3/1997 | Froix |
| 5,618,299 A | 4/1997 | Khosravi et al. |
| 5,629,077 A | 5/1997 | Turnlund et al. |
| 5,631,135 A | 5/1997 | Gryaznov et al. |
| 5,632,771 A | 5/1997 | Boatman et al. |
| 5,632,840 A | 5/1997 | Campbell |
| 5,637,113 A | 6/1997 | Tartaglia et al. |
| 5,649,977 A | 7/1997 | Campbell |
| 5,667,767 A | 9/1997 | Greff et al. |
| 5,667,796 A | 9/1997 | Otten |
| 5,670,558 A | 9/1997 | Onishi et al. |
| 5,693,085 A | 12/1997 | Buirge et al. |
| 5,700,286 A | 12/1997 | Tartaglia et al. |
| 5,707,385 A | 1/1998 | Williams |
| 5,711,763 A | 1/1998 | Nonami et al. |
| 5,716,981 A | 2/1998 | Hunter et al. |
| 5,725,549 A | 3/1998 | Lam |
| 5,726,297 A | 3/1998 | Gryaznov et al. |
| 5,728,751 A | 3/1998 | Patnaik |
| 5,733,326 A | 3/1998 | Tomonto et al. |
| 5,733,330 A | 3/1998 | Cox |
| 5,733,564 A | 3/1998 | Lehtinen |
| 5,733,925 A | 3/1998 | Kunz et al. |
| 5,741,881 A | 4/1998 | Patnaik |
| 5,756,457 A | 5/1998 | Wang et al. |
| 5,756,476 A | 5/1998 | Epstein et al. |
| 5,765,682 A | 6/1998 | Bley et al. |
| 5,766,204 A | 6/1998 | Porter et al. |
| 5,766,239 A | 6/1998 | Cox |
| 5,766,710 A | 6/1998 | Turnlund et al. |
| 5,769,883 A | 6/1998 | Buscemi et al. |
| 5,780,807 A | 7/1998 | Saunders |
| 5,800,516 A | 9/1998 | Fine et al. |
| 5,811,447 A | 9/1998 | Kunz et al. |
| 5,824,049 A | 10/1998 | Ragheb et al. |
| 5,830,178 A | 11/1998 | Jones et al. |
| 5,830,461 A | 11/1998 | Billiar |
| 5,830,879 A | 11/1998 | Isner |
| 5,833,651 A | 11/1998 | Donovan et al. |
| 5,834,582 A | 11/1998 | Sinclair et al. |
| 5,836,962 A | 11/1998 | Gianotti |
| 5,837,313 A | 11/1998 | Ding et al. |
| 5,837,835 A | 11/1998 | Gryaznov et al. |
| 5,840,083 A | 11/1998 | Braach-Maksvytis |
| 5,851,508 A | 12/1998 | Greff et al. |
| 5,853,408 A | 12/1998 | Muni |
| 5,854,207 A | 12/1998 | Lee et al. |
| 5,855,612 A | 1/1999 | Ohthuki et al. |
| 5,855,618 A | 1/1999 | Patnaik et al. |
| 5,858,746 A | 1/1999 | Hubbell et al. |
| 5,865,814 A | 2/1999 | Tuch |
| 5,868,781 A | 2/1999 | Killion |
| 5,873,904 A | 2/1999 | Ragheb et al. |
| 5,874,101 A | 2/1999 | Zhong et al. |
| 5,874,109 A | 2/1999 | Ducheyne et al. |
| 5,874,165 A | 2/1999 | Drumheller |
| 5,876,743 A | 3/1999 | Ibsen et al. |
| 5,877,263 A | 3/1999 | Patnaik et al. |
| 5,879,713 A | 3/1999 | Roth et al. |
| 5,888,533 A | 3/1999 | Dunn |
| 5,891,192 A | 4/1999 | Murayama et al. |
| 5,897,955 A | 4/1999 | Drumheller |
| 5,906,759 A | 5/1999 | Richter |
| 5,914,182 A | 6/1999 | Drumheller |
| 5,916,870 A | 6/1999 | Lee et al. |
| 5,922,005 A | 7/1999 | Richter et al. |
| 5,942,209 A | 8/1999 | Leavitt et al. |
| 5,948,428 A | 9/1999 | Lee et al. |
| 5,954,744 A | 9/1999 | Phan et al. |
| 5,957,975 A | 9/1999 | Lafont et al. |

| Patent No. | Date | Name |
|---|---|---|
| 5,965,720 A | 10/1999 | Gryaznov et al. |
| 5,971,954 A | 10/1999 | Conway et al. |
| 5,976,182 A | 11/1999 | Cox |
| 5,980,564 A | 11/1999 | Stinson |
| 5,980,928 A | 11/1999 | Terry |
| 5,980,972 A | 11/1999 | Ding |
| 5,981,568 A | 11/1999 | Kunz et al. |
| 5,986,169 A | 11/1999 | Gjunter |
| 5,997,468 A | 12/1999 | Wolff et al. |
| 6,010,445 A | 1/2000 | Armini et al. |
| 6,015,541 A | 1/2000 | Greff et al. |
| 6,042,875 A | 3/2000 | Ding et al. |
| 6,048,964 A | 4/2000 | Lee et al. |
| 6,051,648 A | 4/2000 | Rhee et al. |
| 6,056,993 A | 5/2000 | Leidner et al. |
| 6,060,451 A | 5/2000 | DiMaio et al. |
| 6,063,092 A | 5/2000 | Shin |
| 6,066,156 A | 5/2000 | Yan |
| 6,071,266 A | 6/2000 | Kelley |
| 6,074,659 A | 6/2000 | Kunz et al. |
| 6,080,177 A | 6/2000 | Igaki et al. |
| 6,080,488 A | 6/2000 | Hostettler et al. |
| 6,083,258 A | 7/2000 | Yadav |
| 6,093,463 A | 7/2000 | Thakrar |
| 6,096,070 A | 8/2000 | Ragheb et al. |
| 6,096,525 A | 8/2000 | Patnaik |
| 6,099,562 A | 8/2000 | Ding et al. |
| 6,103,230 A | 8/2000 | Billiar et al. |
| 6,107,416 A | 8/2000 | Patnaik et al. |
| 6,110,188 A | 8/2000 | Narciso, Jr. |
| 6,113,629 A | 9/2000 | Ken |
| 6,117,979 A | 9/2000 | Hendriks et al. |
| 6,120,536 A | 9/2000 | Ding et al. |
| 6,120,904 A | 9/2000 | Hostettler et al. |
| 6,121,027 A | 9/2000 | Clapper et al. |
| 6,125,523 A | 10/2000 | Brown et al. |
| 6,127,173 A | 10/2000 | Eckstein et al. |
| 6,129,761 A | 10/2000 | Hubbell |
| 6,129,928 A | 10/2000 | Sarangapani et al. |
| 6,150,630 A | 11/2000 | Perry et al. |
| 6,153,252 A | 11/2000 | Hossainy et al. |
| 4,776,337 A | 12/2000 | Palmaz |
| 6,159,951 A | 12/2000 | Karpeisky et al. |
| 6,160,084 A | 12/2000 | Langer et al. |
| 6,165,212 A | 12/2000 | Dereume et al. |
| 6,166,130 A | 12/2000 | Rhee et al. |
| 6,169,170 B1 | 1/2001 | Gryaznov et al. |
| 6,171,609 B1 | 1/2001 | Kunz |
| 6,174,330 B1 | 1/2001 | Stinson |
| 6,177,523 B1 | 1/2001 | Reich et al. |
| 6,183,505 B1 | 2/2001 | Mohn, Jr. et al. |
| 6,187,045 B1 | 2/2001 | Fehring et al. |
| 6,187,054 B1 * | 2/2001 | Colone et al. ............... 128/898 |
| 6,210,715 B1 | 4/2001 | Starling et al. |
| 6,224,626 B1 | 5/2001 | Steinke |
| 6,228,845 B1 | 5/2001 | Donovan et al. |
| 6,240,616 B1 | 6/2001 | Yan |
| 6,245,076 B1 | 6/2001 | Yan |
| 6,245,103 B1 | 6/2001 | Stinson |
| 6,248,344 B1 | 6/2001 | Ylanen et al. |
| 6,251,135 B1 | 6/2001 | Stinson et al. |
| 6,251,142 B1 | 6/2001 | Bernacca et al. |
| 6,273,913 B1 | 8/2001 | Wright et al. |
| 6,281,262 B1 | 8/2001 | Shikinami |
| 6,284,333 B1 | 9/2001 | Wang et al. |
| 6,287,332 B1 | 9/2001 | Bolz et al. |
| 6,290,721 B1 | 9/2001 | Heath |
| 6,293,966 B1 | 9/2001 | Frantzen |
| 6,303,901 B1 | 10/2001 | Perry et al. |
| 6,312,459 B1 | 11/2001 | Huang et al. |
| 6,327,772 B1 | 12/2001 | Zadno-Azizi et al. |
| 4,733,665 C2 | 1/2002 | Palmaz |
| 6,375,826 B1 | 4/2002 | Wang et al. |
| 6,379,334 B1 * | 4/2002 | Frassica ................. 604/165.04 |
| 6,379,381 B1 | 4/2002 | Hossainy et al. |
| 6,387,117 B1 | 5/2002 | Arnold et al. |
| 6,387,121 B1 | 5/2002 | Alt |
| 6,388,043 B1 | 5/2002 | Langer et al. |
| 6,395,326 B1 | 5/2002 | Castro et al. |
| 6,409,761 B1 | 6/2002 | Jang |
| 6,423,092 B2 | 7/2002 | Datta et al. |
| 6,461,632 B1 | 10/2002 | Gogolewski |
| 6,464,720 B2 | 10/2002 | Boatman et al. |
| 6,479,565 B1 | 11/2002 | Stanley |
| 6,485,512 B1 | 11/2002 | Cheng |
| 6,492,615 B1 | 12/2002 | Flanagan |
| 6,494,908 B1 | 12/2002 | Huxel et al. |
| 6,495,156 B2 | 12/2002 | Wenz et al. |
| 6,511,748 B1 | 1/2003 | Barrows |
| 6,517,888 B1 | 2/2003 | Weber |
| 6,527,801 B1 | 3/2003 | Dutta |
| 6,537,589 B1 | 3/2003 | Chae et al. |
| 6,539,607 B1 | 4/2003 | Fehring et al. |
| 6,540,777 B2 | 4/2003 | Stenzel |
| 6,554,854 B1 | 4/2003 | Flanagan |
| 6,565,599 B1 | 5/2003 | Hong et al. |
| 6,569,191 B1 | 5/2003 | Hogan |
| 6,569,193 B1 | 5/2003 | Cox et al. |
| 6,572,672 B2 | 6/2003 | Yadav et al. |
| 6,574,851 B1 | 6/2003 | Mirizzi |
| 6,585,755 B2 | 7/2003 | Jackson et al. |
| 6,592,614 B2 | 7/2003 | Lenker et al. |
| 6,592,617 B2 | 7/2003 | Thompson |
| 6,613,072 B2 | 9/2003 | Lau et al. |
| 6,620,191 B1 | 9/2003 | Svensson |
| 6,626,939 B1 | 9/2003 | Burnside et al. |
| 6,629,350 B2 | 10/2003 | Motsenbocker |
| 6,635,269 B1 | 10/2003 | Jennissen |
| 6,645,243 B2 | 11/2003 | Vallana et al. |
| 6,656,162 B2 | 12/2003 | Santini, Jr. et al. |
| 6,664,335 B2 | 12/2003 | Krishnan |
| 6,666,214 B2 | 12/2003 | Canham |
| 6,667,049 B2 | 12/2003 | Janas et al. |
| 6,669,723 B2 | 12/2003 | Killion et al. |
| 6,676,697 B1 | 1/2004 | Richter |
| 6,679,980 B1 | 1/2004 | Andreacchi |
| 6,689,123 B2 | 2/2004 | Pinchasik |
| 6,689,375 B1 | 2/2004 | Wahlig et al. |
| 6,695,920 B1 | 2/2004 | Pacetti et al. |
| 6,706,273 B1 | 3/2004 | Roessler |
| 6,709,379 B1 | 3/2004 | Brandau et al. |
| 6,719,934 B2 | 4/2004 | Stinson |
| 6,719,989 B1 | 4/2004 | Matsushima et al. |
| 6,720,402 B2 | 4/2004 | Langer et al. |
| 6,726,713 B2 | 4/2004 | Schaldach et al. |
| 6,746,773 B2 | 6/2004 | Llanos et al. |
| 6,752,826 B2 | 6/2004 | Holloway et al. |
| 6,752,829 B2 * | 6/2004 | Kocur et al. ............... 623/1.42 |
| 6,753,007 B2 | 6/2004 | Haggard et al. |
| 6,764,505 B1 | 7/2004 | Hossainy et al. |
| 6,818,063 B1 | 11/2004 | Kerrigan |
| 6,823,576 B2 | 11/2004 | Austin |
| 6,846,323 B2 | 1/2005 | Yip et al. |
| 7,329,366 B1 * | 2/2008 | Gale et al. .................... 216/88 |
| 2001/0044652 A1 | 11/2001 | Moore |
| 2002/0002399 A1 | 1/2002 | Huxel et al. |
| 2002/0004060 A1 | 1/2002 | Heublein et al. |
| 2002/0004101 A1 | 1/2002 | Ding et al. |
| 2002/0062148 A1 | 5/2002 | Hart |
| 2002/0065553 A1 | 5/2002 | Weber |
| 2002/0111590 A1 | 8/2002 | Davila et al. |
| 2002/0116050 A1 | 8/2002 | Kocur |
| 2002/0138133 A1 | 9/2002 | Lenz et al. |
| 2002/0161114 A1 | 10/2002 | Gunatillake et al. |
| 2003/0033001 A1 | 2/2003 | Igaki |
| 2003/0093107 A1 | 5/2003 | Parsonage et al. |

| | | | |
|---|---|---|---|
| 2003/0100865 | A1 | 5/2003 | Santini, Jr. et al. |
| 2003/0105518 | A1 | 6/2003 | Dutta |
| 2003/0105530 | A1 | 6/2003 | Pirhonen |
| 2003/0171053 | A1 | 9/2003 | Sanders |
| 2003/0187495 | A1 | 10/2003 | Cully et al. |
| 2003/0208259 | A1 | 11/2003 | Penhasi |
| 2003/0209835 | A1 | 11/2003 | Chun et al. |
| 2003/0226833 | A1 | 12/2003 | Shapovalov et al. |
| 2003/0236563 | A1 | 12/2003 | Fifer |
| 2004/0093077 | A1 | 5/2004 | White et al. |
| 2004/0098095 | A1 | 5/2004 | Burnside et al. |
| 2004/0111149 | A1 | 6/2004 | Stinson |
| 2004/0127970 | A1 | 7/2004 | Saunders et al. |
| 2004/0143317 | A1 | 7/2004 | Stinson et al. |
| 2004/0167610 | A1 | 8/2004 | Fleming, III |
| 2005/0187615 | A1* | 8/2005 | Williams et al. ............ 623/1.34 |
| 2006/0047336 | A1* | 3/2006 | Gale et al. ................. 623/1.11 |

FOREIGN PATENT DOCUMENTS

| | | |
|---|---|---|
| DE | 197 31 021 | 1/1999 |
| DE | 198 56 983 | 12/1999 |
| EP | 0 108 171 | 5/1984 |
| EP | 0 144 534 | 6/1985 |
| EP | 0 364 787 | 4/1990 |
| EP | 0 397 500 | 11/1990 |
| EP | 0 464 755 | 1/1992 |
| EP | 0 493 788 | 7/1992 |
| EP | 0 554 082 | 8/1993 |
| EP | 0 578 998 | 1/1994 |
| EP | 0 604 022 | 6/1994 |
| EP | 0 621 017 | 10/1994 |
| EP | 0 623 354 | 11/1994 |
| EP | 0 665 023 | 8/1995 |
| EP | 0 709 068 | 5/1996 |
| EP | 0 970 711 | 1/2000 |
| GB | 2 247 696 | 3/1992 |
| JP | 2004-261567 A * | 9/2004 |
| WO | WO 89/03232 | 4/1989 |
| WO | WO 90/01969 | 3/1990 |
| WO | WO 90/04982 | 5/1990 |
| WO | WO 90/06094 | 6/1990 |
| WO | WO 91/17744 | 11/1991 |
| WO | WO 91/17789 | 11/1991 |
| WO | WO 92/10218 | 6/1992 |
| WO | WO 93/06792 | 4/1993 |
| WO | WO 94/21196 | 9/1994 |
| WO | WO 95/29647 | 11/1995 |
| WO | WO 98/04415 | 2/1998 |
| WO | WO 99/03515 | 1/1999 |
| WO | WO 99/16386 | 4/1999 |
| WO | WO 99/42147 | 8/1999 |
| WO | WO 00/12147 | 3/2000 |
| WO | WO 00/64506 | 11/2000 |
| WO | WO 01/01890 | 1/2001 |
| WO | WO 2004/023985 | 3/2004 |

OTHER PUBLICATIONS

Anonymous, *Bioabsorbable stent mounted on a catheter having optical coherence tomography capabilities*, Research Disclosure, Sep. 2004, pp. 1159-1162.
Ansari, *End-to-end tubal anastomosis using an absorbable stent*, Fertility and Sterility, vol. 32(2), pp. 197-201 (Aug. 1979).
Ansari, *Tubal Reanastomosis Using Absorbable Stent*, International Journal of Fertility, vol. 23, No. 4, pp. 242-243 (1978).
Bull, *Parylene Coating for Medical Applications*, Medical Product Manufacturing News 18,1 pg. (Mar. 1993).
Casper et al., *Fiber-Reinforced Absorbable Composite for Orthopedic Surgery*, Polymeric Materials Science and Engineering, 53: pp. 497-501 (1985).
Detweiler et al., *Gastrointestinal Sutureless Anastomosis Using Fibrin Glue: Reinforcement of the Sliding Absorbable Intraluminal Nontoxic Stent and Development of a Stent Placement Device*, Journal of Investigative Surgery, vol. 9(2), pp. 111-130 (Mar./Apr. 1996).
Detweiler et al., *Sliding, Absorbable, Reinforced Ring and an Axially Driven Stent Placement Device for Sutureless Fibrin Glue Gastrointestinal Anastomisis*, Journal of Investigative Surgery, vol. 9(6), pp. 495-504 (Nov./Dec. 1996).
Detweiler et al., *Sutureless Anastomosis of the Small Intestine and the Colon in Pigs Using an Absorbable Intraluminal Stent and Fibrin Glue*, Journal of Investigative Surgery, vol. 8(2), pp. 129-140 (Mar. 1995).
Detweiler et al., *Sutureless Cholecystojejunostomy in Pigs Using an Absorbable Intraluminal Stent and Fibrin Glue*, Journal of Investigative Surgery, vol. 9(1), pp. 13-26 (Jan./Feb. 1996).
Devanathan et al., *Polymeric Conformal Coatings for Implantable Electronic Devices*, IEEE Transactions on Biomedical Engineering, vol. BME-27(11), pp. 671-675 (1980).
Elbert et al., *Conjugate Addition Reactions Combined with Free-Radical Cross-Linking for the Design of Materials for Tissue Engineering*, Biomacromolecules 2, pp. 430-441 (2001).
Hahn et al., *Biocompatibility of Glow-Discharge-Polymerized Films and Vacuum-Deposited Parylene*, J Applied Polymer Sci, 38, pp. 55-64 (1984).
Hahn et al., *Glow Discharge Polymers as Coatings for Implanted Devices*, ISA, pp. 109-111 (1981).
He et al., *Assessment of Tissue Blood Flow Following Small Artery Welding with an Intraluminal Dissolvable Stent*, Microsurgery, vol. 19(3), pp. 148-152 (1999).
Kelley et al., *Totally Resorbable High-Strength Composite Material*, Advances in Biomedical Polymers, 35, pp. 75-85 (1987).
Kubies et al., *Microdomain Structure In polylactide-block-poly(ethylene oxide) copolymer films*, Biomaterials 21 pp. 529-536 (2000).
Kutryk et al., *Coronary Stenting: Current Perspectives*, a companion to the Handbook of Coronary Stents pp. 1-16 (1999).
Martin et al., *Enhancing the biological activity of immobilized osteopontin using a type-1 collagen affinity coating*, J. Biomed. Mater Res 70A, pp. 10-19 (2004).
Mauduit et al., *Hydrolytic degradation of films prepared from blends of high and low molecular weight poly(DL-lactic acid)s*, J. Biomed. Mater. Res. v. 30, pp. 201-207 (1996).
Middleton et al., *SynthetiC biodegradable polymers as orthopedic devices*, Biomaterials, vol. 21, pp. 2335-2346 (2000).
Muller et al., *Advances in Coronary Angioplasty: Endovascular Stents*, Coron. Arter. Dis., 1(4), pp. 438-448 (Jul./Aug. 1990).
Nichols et al., *Electrical Insulation of Implantable Devices by Composite Polymer Coatings*, ISA Transactions, 26(4), pp. 15-18 (1987).
Peuster et al., *A novel approach to temporary stenting: degradable cardiovascular stents produced from corrodible metal-results 6-18 months after implantation into New Zealand white rabbits*, Heart 86, pp. 563-569 (2001).
Pietrzak et al., *Bioabsorbable Fixation Devices: Status for the Craniomaxillofacial Surgeon*, J. Craniofaxial Surg. 2, pp. 92-96 (1997).
Pietrzak et al., *Bioresorbable implants—practical considerations*, Bone v. 19, No. 1, Supplement Jul. 1996: 109S-119S.
Redman, *Clinical Experience with Vasovasostomy Utilizing Absorbable Intravasal Stent*, Urology, vol. 20(1), pp. 59-61 (Jul. 1982).
Rust et al., *The Effect of Absorbable Stenting on Postoperative Stenosis of the Surgically Enlarged Maxillary Sinus Ostia in a Rabbit Animal Model*, Archives of Otolaryngology, vol. 122(12) pp. 1395-1397 (Dec. 1996).
Schatz, *A View of Vascular Stents*, Circulation, 79(2), pp. 445-457 (Feb. 1989).
Schmidt et al., *Long-Term Implants of Parylene-C Coated Microelectrodes*, Med & Biol Eng & Comp, 26(1), pp. 96-101 (Jan. 1988).
Spagnuolo et al., *Gas 1 is induced by VE-cadherin and vascular endothelial growth factor and inhibits endothelial cell apoptosis*, Blood 103, pp. 3005-3012 (2004).
Tamai et al., *Initial and 6-Month Results of Biodegradable Poly-l-Lactic Acid Coronary Stents in Humans*, Circulation, pp. 399-404 (Jul. 25, 2000).
Tsuji et al., *Biodegradable Polymeric Stents*, Current Interventional Cardiology Reports 3, pp. 10-17 (2001).

Völkel et al., *Targeting of immunoliposomes to endothelial cells using a single-chain Fv fragment directed against human endoglin (CD105)*, Biochimica et Biophysica Acta 1663, pp. 158-166 (2004).

von Recum et al., *Degradation of polydispersed poly(L-lactic acid) to modulate lactic acid release*, Biomaterials 16, pp. 441-445 (1995).

Yau et al., *Modern Size-Exclusion Liquid Chromatography*, Wiley-Interscience Publication, IX-XV (1979).

U.S. Appl. No. 10/931,853, filed Aug. 31, 2004, Hossainy et al.

* cited by examiner

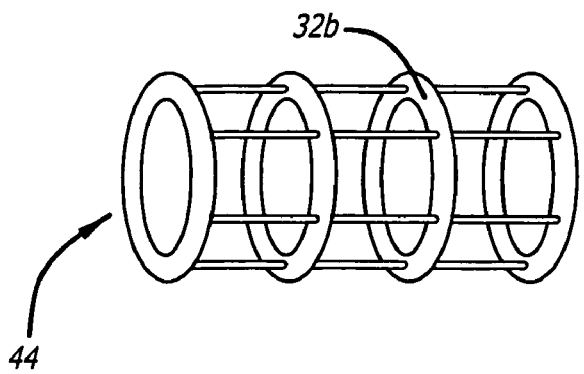
FIG. 5
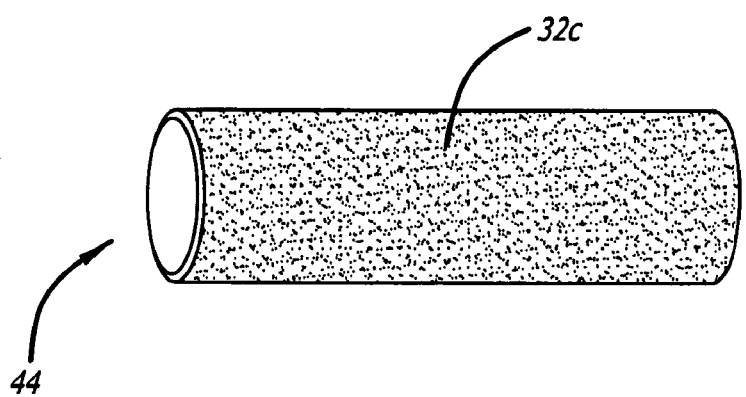
FIG. 6
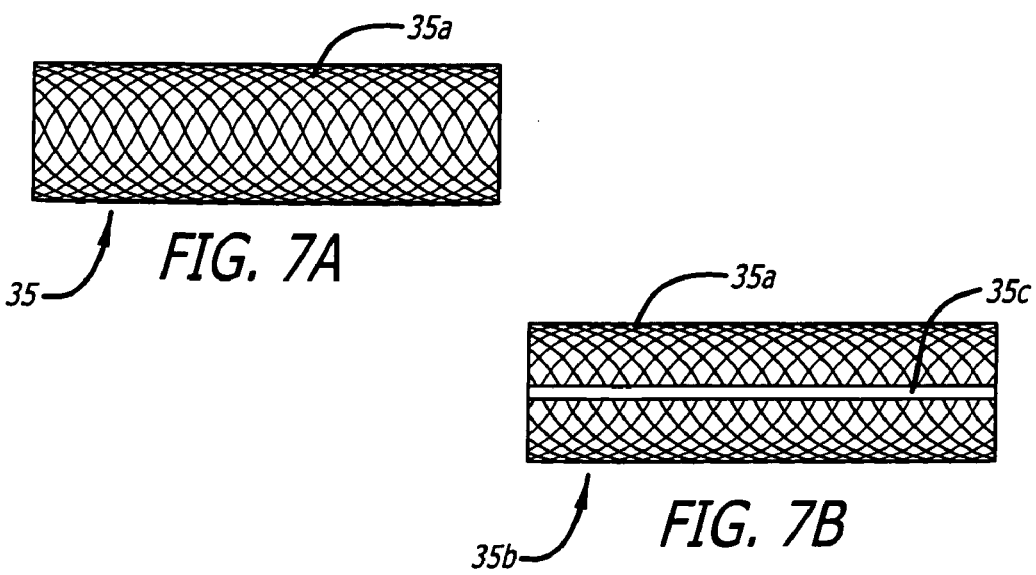
FIG. 7A
FIG. 7B

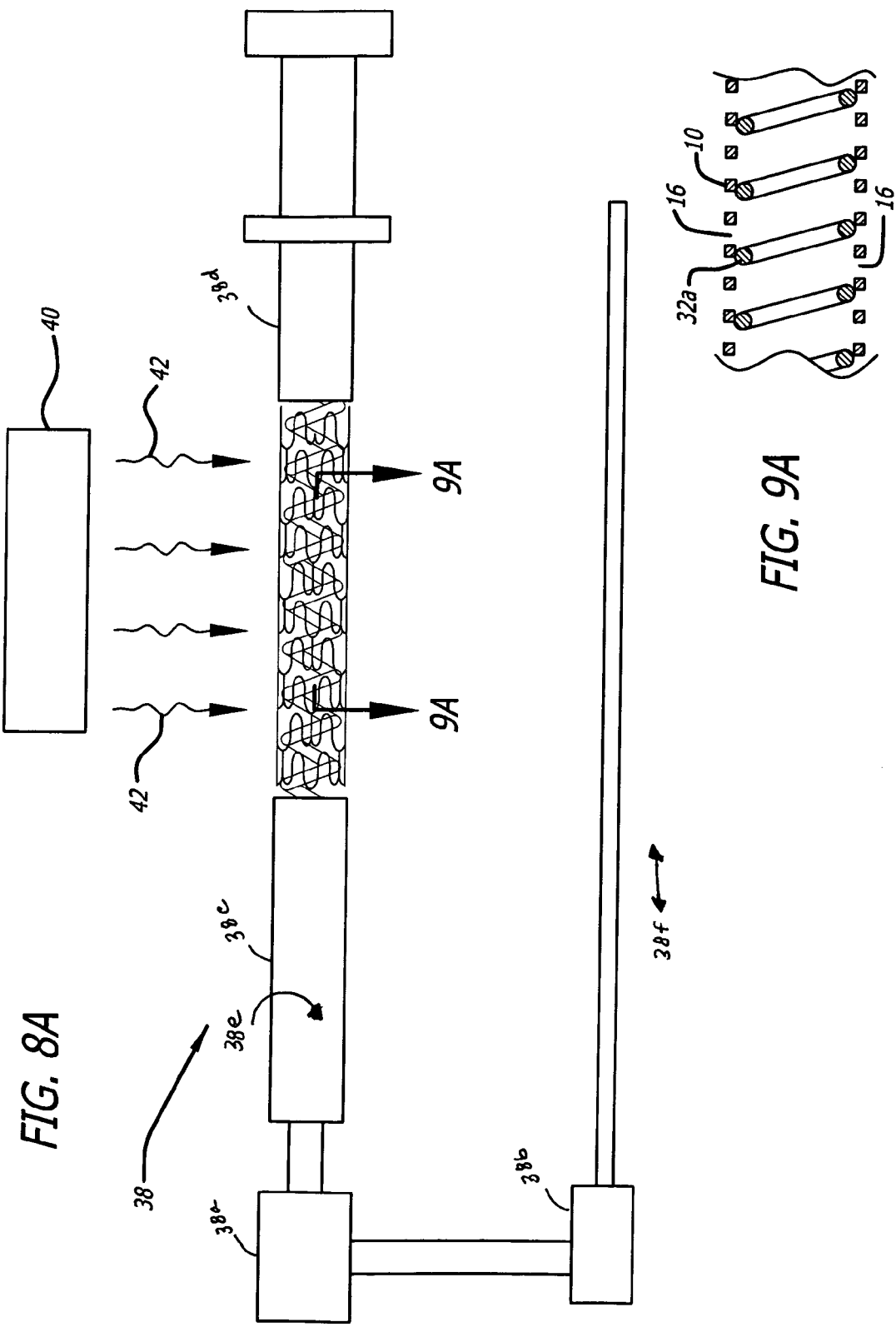

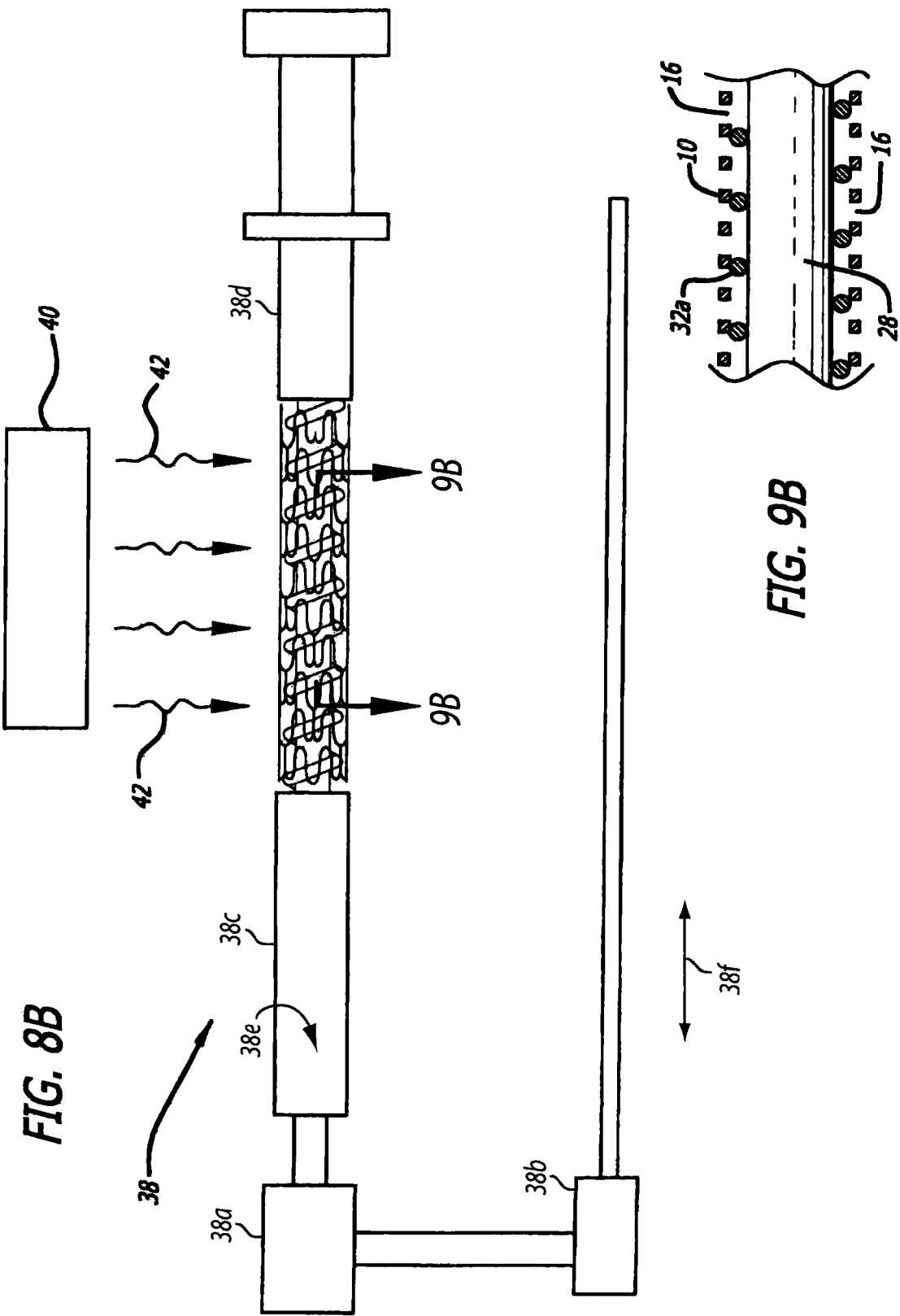

POLYMERIC STENT POLISHING METHOD AND APPARATUS

BACKGROUND OF THE INVENTION

The present invention relates generally to methods of and apparatuses for polishing radially expandable endoprothesis adapted to be implanted in a lumen of a tubular organ. A "lumen" refers to a cavity of a tubular organ such as a blood vessel. Endoprostheses correspond to artificial implantable medical devices that are placed inside the body, and stents are examples of these endoprostheses. Stents are generally cylindrically shaped devices which function to hold open and sometimes expand a segment of a blood vessel or other anatomical lumens such as urinary tracts and bile ducts. Stents are often used in the treatment of atherosclerotic stenosis in blood vessels. "Stenosis" refers to a narrowing or constriction of the diameter of a body passage or orifice. In such treatments, stents reinforce vessels and prevent restenosis following angioplasty in the vascular system. "Restenosis" refers to the reoccurrence of stenosis in a blood vessel or heart valve after it has been treated (as by balloon angioplasty or valvuloplasty) with apparent success.

A treatment involving a stent includes both delivery and deployment of the stent. "Delivery" refers to introducing and transporting the stent through a lumen of a tubular organ to a region requiring treatment. "Deployment" corresponds to the expanding of the stent within the lumen at the treatment region. Delivery and deployment of a stent may be accomplished by positioning the stent about one end of a catheter, inserting the end of the catheter through the skin into the lumen, advancing the catheter in the lumen to a desired treatment location, expanding the stent at the treatment location, and then removing the catheter from the lumen.

In the case of a balloon-expandable stent, the stent is mounted about a balloon disposed on the catheter. Mounting the stent typically involves compressing, or crimping, the stent onto the balloon. The stent is then expanded by inflating the balloon. The balloon may then be deflated and the catheter withdrawn. In the case of a self-expanding stent, the stent may be secured to the catheter via a retractable sheath or a sock. When the stent is in a desired body location, the sheath may be withdrawn allowing the stent to self-expand.

Stents have been made of many materials including metals and polymers. Polymer materials include both nonbioerodable and bioerodable plastic materials. In some applications, a polymeric bioerodable stent may be more advantageous than a metal stent due to its biodegradeability and greater flexibility relative to the metal stent. The cylindrical structure of a stent is typically composed of a scaffolding that includes a pattern or network of interconnecting structural elements or struts. The scaffolding can be formed from wires, tubes, or planar films of material rolled into a cylindrical shape. In addition, a medicated stent may be fabricated by coating the surface of either a metallic or polymeric scaffolding with a polymeric carrier. The polymeric carrier can include an active agent or drug. Furthermore, the pattern that makes up the stent allows the stent to be radially expandable and longitudinally flexible. Longitudinal flexibility facilitates delivery of the stent and rigidity functions to hold open a lumen of a tubular organ. Generally, the pattern should be designed to maintain the longitudinal flexibility and rigidity required of the stent. The stent should also have adequate strength in the circumferential direction.

A number of techniques have been suggested for the fabrication of stents from tubes and planar films or sheets. Examples of such techniques include laser cutting or etching a pattern onto a material. Laser cutting may be performed on a planar film of a material which is then rolled into a tubular configuration. Alternatively, a desired pattern may be etched directly onto a tube. Other techniques involve cutting a desired pattern into a sheet or a tube via chemical etching or electrical discharge machining. Laser cutting of stents has been described in a number of publications including U.S. Pat. No. 5,780,807 to Saunders, U.S. Pat. No. 5,922,005 to Richter and U.S. Pat. No. 5,906,759 to Richter.

With respect to polymeric stents, a number of manufacturing methods have been employed. In one method, the polymeric stent may be formed by laser cutting a flat polymeric sheet in the form of rings and links, subsequently rolling the pattern into the shape of the cylindrical stent and then providing a longitudinal weld to form the stent. In another method, a flat polymeric sheet may be chemically etched and then subsequently rolled and welded to form the polymeric stent. Additionally, a polymeric wire may be coiled to form a polymeric stent. In yet another method, a polymeric stent may be formed from a tube by laser cutting a pattern of cylindrical rings and connecting rings in the tube itself. See, e.g., U.S. Pat. No. 6,585,755 to Jackson et al.

In the manufacturing processes previously described, a resultant "rough" stent will be produced. That is, the struts forming the stent will typically have an approximate "square" cross-section with four distinct surfaces as a result of the cutting or etching process. A typical stent is then polished to "round out" the sharp corners in addition to smoothing out the surface of the stent.

Various methods exist for polishing metal stents. Typical polishing methods include electropolishing using an electrolyte solution or laser polishing using a laser, described in more detail in U.S. Pat. No. 5,344,425 to Sawyer, U.S. Pat. No. 6,679,980 to Andreacchi, U.S. Pat. No. 6,375,826 to Wang et al. and U.S. Pat. No. 6,492,615 to Flanagan. The use of abrasives to polish stents is disclosed in U.S. Pat. No. 5,746,691 to Frantzen, U.S. Pat. No. 5,788,558 to Klein and U.S. Pat. No. 6,086,455 to Frantzen.

Polymeric stents may undergo polishing as well. A polymeric stent may be polished using solvents. Solvent polishing smoothes out the surfaces and rounds out "sharp corners" of the struts and connecting elements of a polymeric stent; however, adequately removing the solvent and minimizing the residual solvent are problems associated with this method. Accordingly, methods are needed for polishing polymeric stents.

SUMMARY OF THE INVENTION

Methods for simultaneously polishing the abluminal surface and the luminal surface of an implantable medical device are disclosed herein. The implantable device may be a metal or polymeric stent, for example. The polymeric stent may be a bioerodable, biodegradable or bioadsorbable polymer. In one embodiment, a wire is wrapped around the abluminal surface of a mandrel (of a stent manufacturing device), and the mandrel is thereafter removed forming a hollow spiral-mandrel (or helical-mandrel). An unpolished stent is then mounted onto the abluminal surface of the hollow spiral-mandrel. The stent is then subjected to heat treatment, such as heat flashing from a heat source, resulting in substantially or completely smooth surfaces and rounded corners of the unpolished stent struts and connecting elements on both the abluminal and luminal surfaces of the stent thereof.

The hollow spiral-mandrel allows heat to pass between the spaced coils of the spiral-mandrel so that the heat reaches the luminal surface of the stent. As a result, the abluminal surface and luminal surface of the stent are simultaneously polished. That is, the spiral-mandrel promotes heat transfer to ensure that all four corners of a strut or connecting element are simultaneously rounded out.

In another aspect of the invention, a porous sheath is used in a process to simultaneously polish the abluminal surface and luminal surface of the stent. The sheath serves the same function as that described for the spiral-mandrel, namely, to allow heat to pass through the pores of the porous sheath so that the heat may reach the luminal surface of the stent. It should be understood that the present invention encompasses a variety of different embodiments of the device which provides adequate heat transfer to the luminal surface of the stent for polishing of "sharp corners" therein.

According to another aspect of the invention, a method of polishing a polymeric stent includes: providing a structure with a series of gaps, the structure having an inner surface, an outer surface and a lumen; mounting a stent, the stent having a stent inner surface, a stent outer surface and a stent lumen, onto the structure; and after the mounting, subjecting the stent to heat from a heat source. The heat polishes both the inner and outer surfaces of the polymeric stent. The structure can be, for example, tubular.

According to a further aspect of the invention, a method of polishing a polymeric stent includes: mounting a polymeric stent on a spiral-mandrel; and after the mounting, subjecting the stent to heat from a heat source.

According to a still further aspect of the invention, a method of reducing the stress concentration on angles of struts on a polymeric stent includes: positioning a stent on a spiral-mandrel, the stent including a plurality of struts, the struts having an approximate square cross-section; and after the positioning, applying heat to a surface of the stent from a heat source to smooth out the angles or corners of the struts. The heat can be distributed evenly across the body of the stent or can be specifically directed or concentrated at particular areas of the stent. A concentrated application is preferable when some areas need more polishing than other sections of the stent.

According to a yet another aspect of the invention, a method for simultaneously polishing an entire surface of a polymeric stent includes: wrapping a wire around a mandrel to form a spiral-mandrel; after the wrapping, removing the mandrel from the spiral-mandrel; mounting an unpolished stent on the spiral-mandrel, the stent including a luminal surface, and an abluminal surface; and after the mounting, subjecting the stent to intense heat from a heat source, so that the luminal surface and the abluminal surface are polished.

According to a further aspect of the invention, a method of heat polishing a tubular medical device includes: subjecting a tubular medical device, which is positioned on and around a mandrel having a solid mandrel surface and at least one spacer on the mandrel surface to hold the device spaced out from the mandrel surface, to external heat, such that the heat passes through openings in the device and heat polishes internal surfaces of the device spaced out from the mandrel surface.

According to yet another aspect of the invention, a device for heat polishing an inner surface of a stent includes: a helical structure having an outer surface, an inner surface and a lumen, the helical structure including a series of coils. The helical structure can include a series of spaces in between the series of coils, and there are at least two coils. In some embodiments, there are at least three to ten coils, and can be more than ten coils. The spacing between the coils can be at least 0.005". In some embodiments, the device can have a braided configuration, an interconnected ring configuration or a porous tube configuration.

According to a further aspect of the invention, equipment for polishing luminal surfaces of a medical device includes: a means for holding the device relative to a heat source such that the heat can access luminal surfaces of the device. In some embodiments, the device can be a polymeric stent. The equipment can include means for moving the device axially and/or rotationally relative to the source. Further, the equipment can include a conveyor for conveying the device past the source, and the source can be a heat chamber. In some embodiments, the heat source can encircle the device.

Other objects and advantages of the present invention will become more apparent to those persons having ordinary skill in the art to which the present invention pertains from the foregoing description taken in conjunction with the accompanying drawings.

BRIEF DESCRIPTION OF THE DRAWINGS

FIG. 5 illustrates another embodiment of a mandrel of the present invention.

FIG. 6 illustrates yet another embodiment of a mandrel of the present invention.

FIG. 7A illustrates yet another embodiment of a mandrel of the present invention.

FIG. 7B illustrates a variation of the mandrel of FIG. 7A.

FIG. 8A illustrates an embodiment of a method of the present invention in which a stent is mounted on the spiral-mandrel of FIG. 4C for polishing thereof.

FIG. 8B illustrates an embodiment of a method of the present invention in which a stent is mounted on the spiral-mandrel assembly of FIG. 4B for polishing thereof.

FIG. 9A is an enlarged cross-sectional view taken on line 9A-9A of FIG. 8A of the mandrel of FIG. 4C with a stent mounted thereon.

FIG. 9B is an enlarged cross-sectional view taken on line 9B-9B of FIG. 8B of the spiral-mandrel of FIG. 4B with a stent mounted thereon.

DETAILED DESCRIPTION OF PREFERRED EMBODIMENTS OF THE INVENTION

Figure 1:
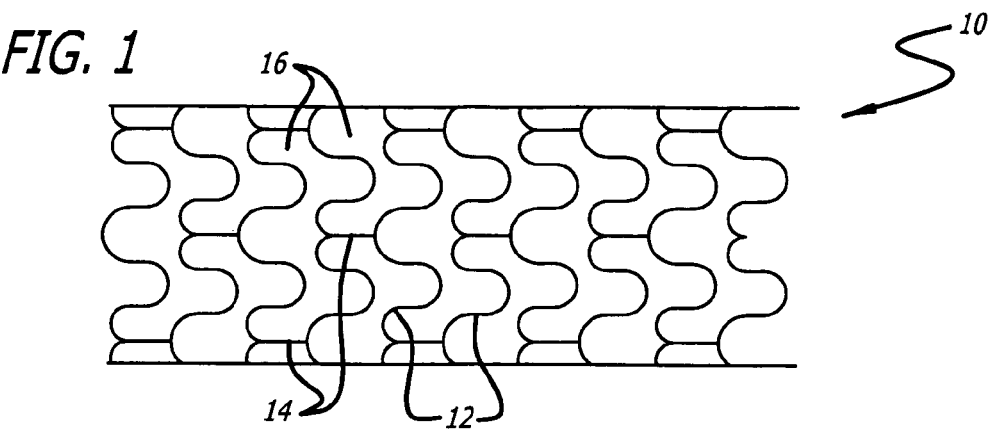
FIG. 1 illustrates an unpolished stent which can be used pursuant to methods and apparatuses of the present invention.

FIG. 1 illustrates a stent 10, which may be metal or polymeric, preferably polymeric. In either form, the stent 10 can includes a multitude of struts 12 and connecting elements 14, with interstitial spaces 16 located therebetween. Additionally, with respect to a stent constructed from polymer material, the stent 10 may be manufactured by a variety methods, including but not limited to: (a) laser-cutting a flat polymeric sheet in the form of rings and links, and then subsequently rolling the pattern into the shape of the cylindrical stent and providing a longitudinal weld to form the stent; (b) chemically etching a flat polymeric sheet and then subsequently rolling and welding to form the polymeric stent; (c) coiling a polymeric wire to form a polymeric stent, and (d) laser-cutting a pattern of cylindrical rings and connecting rings onto the tube itself. See, e.g., U.S. Pat. No. 6,585,755 to Jackson et al. It has been found, however, that polymeric stents manufactured by conventional polishing processes may be susceptible to cracking.

A polymeric stent 10 can be made from and/or coated with a biostable polymer or a bioerodable, biodegradable, bioadsorbable polymer or any combination thereof. Bioerodable, biodegradable or bioadsorbable are intended to be used interchangeably unless otherwise indicated. Additionally, the length of the stent may vary. In general, a coronary stent will be in a range from eight mm to thirty-eight mm. In one embodiment, the stent 10 may be twelve mm in length. Peripheral stents (being larger vessels) can be as long as one-hundred and fifty mm. Also, the stent inner diameter ("ID") can range anywhere between two mm to four mm for coronary stents and five mm to twenty mm for peripheral stents. In some embodiments, a polymeric stent can include other materials, such as layers or deposits of metallic material which can be bioerodable.

Representative examples of polymers which may comprise a polymeric stent and/or a coating thereon are, but are not limited to, fluorinated polymers or copolymers such as poly(vinylidene fluoride), poly(vinylidene fluoride-co-hexafluoropropene), poly(tetrafluoroethylene), and expanded poly(tetrafluoroethylene); poly(sulfone); poly(N-vinyl pyrrolidone); poly(aminocarbonates); poly(iminocarbonates); poly(anhydride-co-imides), poly(hydroxyvalerate); poly(L-lactic acid); poly(L-lactide); poly(caprolactones); poly(lactide-co-glycolide); poly(hydroxybutyrates); poly(hydroxybutyrate-co-valerate); poly(dioxanones); poly(orthoesters); poly(anhydrides); poly(glycolic acid); poly(glycolide); poly(D,L-lactic acid); poly(D,L-lactide); poly(glycolic acid-co-trimethylene carbonate); poly(phosphoesters); poly(phosphoester urethane); poly(trimethylene carbonate); poly(iminocarbonate); poly(ethylene); and any derivatives, analogs, homologues, congeners, salts, copolymers and combinations thereof.

In some embodiments, the polymers include, but are not limited to, poly(propylene) co-poly(ether-esters) such as, for example, poly(dioxanone) and poly(ethylene oxide)/poly(lactic acid); poly(anhydrides), poly(alkylene oxalates); poly(phosphazenes); poly(urethanes); silicones; poly(esters); poly(olefins); copolymers of poly(isobutylene); copolymers of ethylene-alphaolefin; vinyl halide polymers and copolymers such as poly(vinyl chloride); poly(vinyl ethers) such as, for example, poly(vinyl methyl ether); poly(vinylidene halides) such as, for example, poly(vinylidene chloride); poly(acrylonitrile); poly(vinyl ketones); poly(vinyl aromatics) such as poly(styrene); poly(vinyl esters) such as poly(vinyl acetate); copolymers of vinyl monomers and olefins such as poly(ethylene-co-vinyl alcohol) (EVAL); copolymers of acrylonitrile-styrene, ABS resins, and copolymers of ethylene-vinyl acetate; and any derivatives, analogs, homologues, congeners, salts, copolymers and combinations thereof.

In some embodiments, the materials can also include, but are not limited to, poly(amides) such as Nylon 66 and poly(caprolactam); alkyd resins; poly(carbonates); poly(oxymethylenes); poly(imides); poly(ester amides); poly(ethers) including poly(alkylene glycols) such as, for example, poly(ethylene glycol) and poly(propylene glycol); epoxy resins; polyurethanes; rayon; rayon-triacetate; biomolecules such as, for example, fibrin, fibrinogen, starch, poly(amino acids); peptides, proteins, gelatin, chondroitin sulfate, dermatan sulfate (a copolymer of D-glucuronic acid or L-iduronic acid and N-acetyl-D-galactosamine), collagen, hyaluronic acid, and glycosaminoglycans; other polysaccharides such as, for example, poly(N-acetylglucosamine), chitin, chitosan, cellulose, cellulose acetate, cellulose butyrate, cellulose acetate butyrate, cellophane, cellulose nitrate, cellulose propionate, cellulose ethers, and carboxymethylcellulose; and any derivatives, analogs, homologues, congeners, salts, copolymers and combinations thereof.

In some embodiments, the polymer can be a poly(ester amide), a poly(lactide) or a poly(lactide-co-glycolide) copolymer; and any derivatives, analogs, homologues, congeners, salts, copolymers and combinations thereof.

In some embodiments, the polymers can be biodegradable, bioerodable and/or bioadsorbable. Examples of biodegradable polymers include, but are not limited to, polymers having repeating units such as, for example, an α-hydroxycarboxylic acid, a cyclic diester of an α-hydroxycarboxylic acid, a dioxanone, a lactone, a cyclic carbonate, a cyclic oxalate, an epoxide, a glycol, an anhydride, a lactic acid, a glycolic acid, a lactide, a glycolide, an ethylene oxide, an ethylene glycol, and any derivatives, analogs, homologues, congeners, salts, copolymers and combinations thereof.

In some embodiments, the biodegradable polymers include, but are not limited to, polyesters, poly(ester amides); poly(hydroxyalkanoates) (PHA), amino acids; PEG and/or alcohol groups; polycaprolactones, poly(D-lactide), poly(L-lactide), poly(D,L-lactide), poly(meso-lactide), poly(L-lactide-co-meso-lactide), poly(D-lactide-co-meso-lactide), poly(D,L-lactide-co-meso-lactide), poly(D,L-lactide-co-PEG) block copolymers, poly(D,L-lactide-co-trimethylene carbonate), polyglycolides, poly(lactide-co-glycolide), polydioxanones, polyorthoesters, polyanhydrides, poly(glycolic acid-co-trimethylene carbonate), polyphosphoesters, polyphosphoester urethanes, poly(amino acids), polycyanoacrylates, poly(trimethylene carbonate), poly(imino carbonate), polycarbonates, polyurethanes, copoly(ether-esters) (e.g.

PEO/PLA), polyalkylene oxalates, polyphosphazenes, PHA-PEG, and any derivatives, analogs, homologues, salts, copolymers and combinations thereof.

In other embodiments, the polymers can be poly(glycerol sebacate); tyrosine-derived polycarbonates containing desaminotyrosyl-tyrosine alkyl esters such as, for example, desaminotyrosyl-tyrosine ethyl ester (poly(DTE carbonate)); and any derivatives, analogs, homologues, salts, copolymers and combinations thereof.

In some embodiments, the polymers are selected such that they specifically exclude any one or any combination of any of the polymers taught herein.

Figure 2:
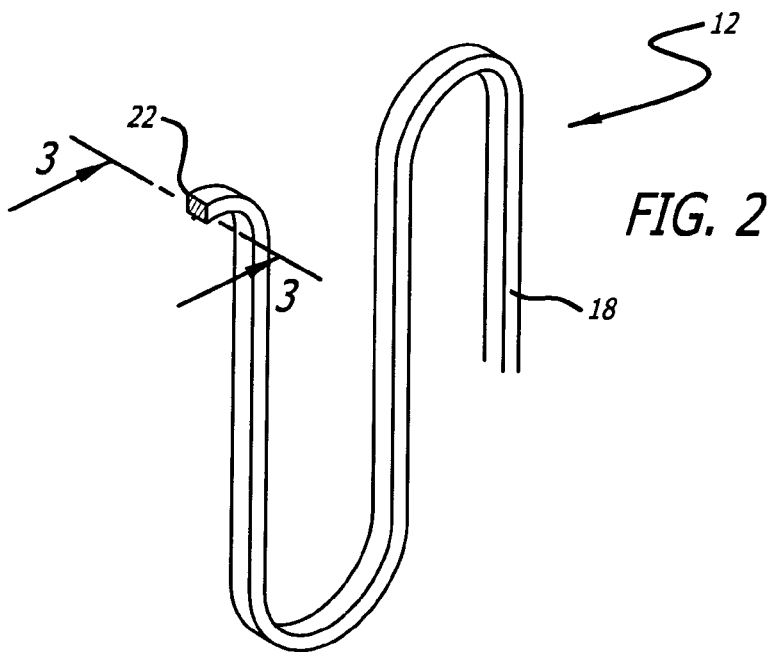
FIG. 2 shows an enlarged portion of a strut of the stent of FIG. 1.

An enlarged portion of a strut 12 of stent 10 is shown in FIG. 2. Before polishing, a cross-section of a typical strut 12 has a "square" shape. That is, in an unpolished state, the strut 12 can include four surfaces, sides or walls 18 with four approximately ninety degree angle "sharp corners" 22. This shape is primarily as a result of the cutting or etching step in the manufacturing process.

Figure 3:
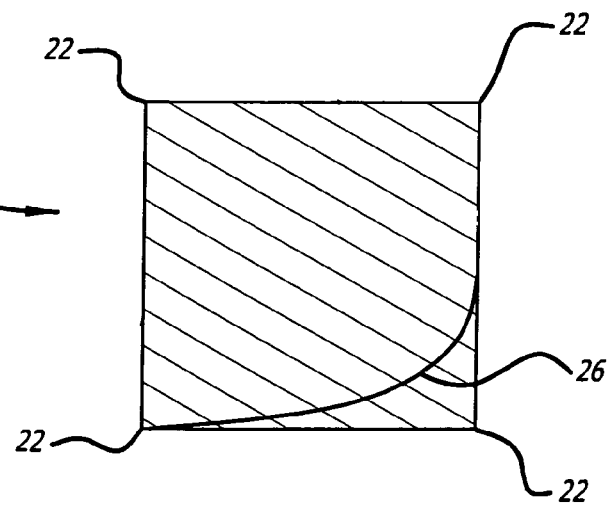
FIG. 3 shows an enlarged cross-sectional view of the strut of FIG. 2 taken on line 3-3.

In FIG. 3, a cross-section of the strut 12 depicted in FIG. 2 is shown taken on line 3-3. If the strut 12 is left unpolished, the sharp corners 22 may result in the manifestation of cracks 26 in the stent 10 when crimped on a catheter or mandrel, or during expansion when delivered into a bodily lumen (see FIGS. 16, 17 and 18, discussed later herein). The cracks 26 are due to the high stress concentration, or "stress risers," initiated from the sharp corners 22. Such cracks may jeopardize the integrity of the stent 10 itself, thereby causing an increased risk of damage to a bodily lumen during delivery of the stent, the collection of plaque and other deposits on the stent and balloon bursts in balloon-expandable stents, for example.

Figure 4A:
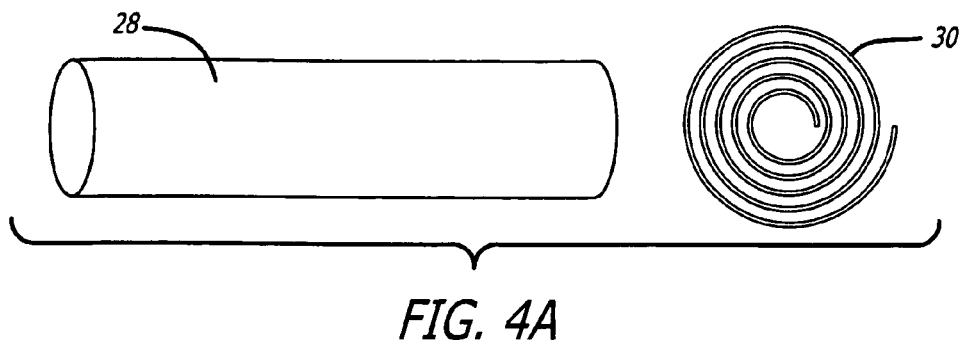
FIG. 4A illustrates a mandrel and coiling wire, which can be used pursuant to the present invention.
Figure 4B:
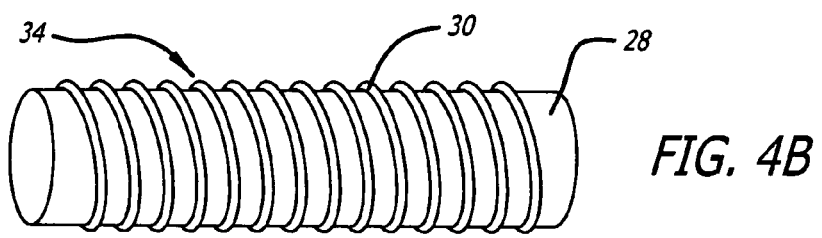
FIG. 4B shows the coiling wire of FIG. 4A wrapped around the mandrel of FIG. 4A.
Figure 4C:
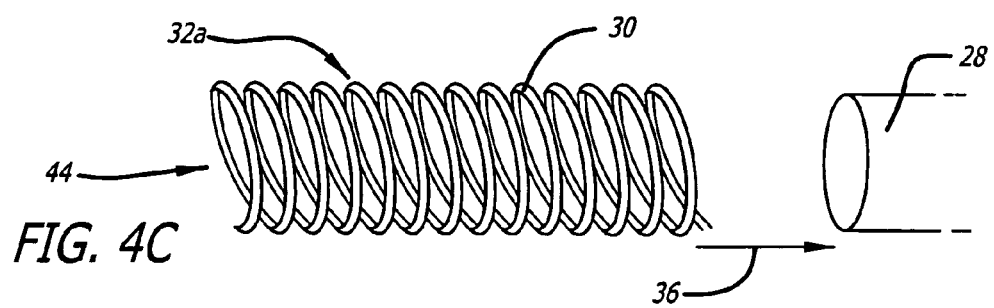
FIG. 4C illustrates a spiral-mandrel formed by coiling the wire around the mandrel of FIG. 4A in accordance with one embodiment of the present invention and subsequently separating the mandrel therefrom.

In general, the present invention is directed to methods of polishing stents to reduce or eliminate stress risers. Thus, FIGS. 4A-4C illustrate one form of creating a "spiral-mandrel" used in one embodiment of a method of polishing a polymeric stent of the present invention. In FIG. 4A, a mandrel 28 and coiling wire 30 are shown. The mandrel 28 may be polymeric or metal, with a typical outer diameter of approximately 0.010" to 0.050". In addition, the coiling wire 30 may be composed of a heat conductive poor heat conductive or non-heat conductive material, or a combination thereof. For example, in one embodiment, the coiling wire 30 may be heat conductive, such as stainless steel, and coated with a non-heat conductive substance, such as parylene. A non-stick coating can also be used, such as Teflon. In another embodiment, the coiling wire 30 may be uncoated stainless steel or titanium, thus retaining heat conductive properties. In some embodiments, the coiling wire can be from or coated with aluminum, copper, silver and/or gold. Additionally, the coiling wire 30 can have a thickness of approximately 0.020" to 0.050", preferably 0.025".

In FIG. 4B, coiling wire 30 is shown wrapped around the mandrel 28 in a helical manner forming a helical assembly 34. A space of approximately 0.005" to 0.050", preferably 0.025", may exist between the coils of the helical assembly 34. In some embodiments, the number of coils may vary from two to fifteen, preferably ten. In other embodiments, the number of coils may be practically unlimited for an embodiment with a continuous mandrel and multiple stents on it similar to a conveyor.

In FIG. 4C, the mandrel 28 is shown being removed from the helical assembly 34 (depicted by arrow 36), resulting in a "spiral-mandrel" 32a with a lumen 44 therein. The spiral-mandrel can be, for example, at least one inch long. The inner diameter of the spiral-mandrel 32a depends on the diameter of the wire 30 used to make it. The outer diameter of the spiral-mandrel 32a depends on the inner diameter of the stent 10. The abluminal surface of the spiral-mandrel 32a can be tightly controlled to match the luminal surface of the unpolished stent 10 in order to provide an appropriate fit between the spiral-mandrel 32a and the stent 10. Ultimately, the spiral-mandrel 32a functions to promote adequate heat transfer to ensure that all four corners 22 of a strut 12 cross-section are properly "rounded out," as will be more fully discussed below.

In an alternative embodiment, a series of interconnected rings 32b with a lumen 44 therein, as illustrated in FIG. 5, may be used as the device to effectuate heat transfer. The interconnected rings 32b can be laser-cut or chemically etched from a pattern of a tube or flat sheet of metal (and rolled into a tube therefore). Alternatively, the rings 32b can be interconnected by a secondary process such as welding. In another alternative embodiment, a porous sheath 32c with a lumen 44 therein, as illustrated in FIG. 6, may be used as the device to effectuate heat transfer. The porous sheath 32c may be manufactured by a variety of methods, including laser-cutting and chemically etching, by methods known to those skilled in the art. Porous sheath 32c can include discrete or interconnected holes that can extend through the body of the sheath 32c so as to provide a passage from the outer surface of the sheath 32c to the lumen 44. This allows the heat to enter and circulate within the lumen 44. Mandrels 32b and 32c can be made or coated with the same materials discussed above.

Referring to FIG. 7A, a further embodiment of the present invention can be a tubular braided device as shown generally at 35 having braided members or "wires" 35a. The criss-crossing wires 35a can be fixed to one another to prevent the braided device from stretching and thereby having its diameter narrow. One way of "fixing" wires 35a is by welding. The braided geometry can be simple or complex by adjusting the angles between wires. An alternative thereof, which is illustrated generally at 35b in FIG. 7B, is also a braided construction but includes longitudinal struts 35c, which can run the length of the braided device or mandrel. The longitudinal struts 35c can act as reinforcement for the criss-crossing wires 35a. Embodiments of FIGS. 5, 6 and 7 can be made from heat conductive, poor heat conductive, non-heat conductive or a combination thereof as discussed above with respect to the spiral mandrel 32a. For example, porous sheath 32c can be made from a heat conductive metal coated with a non-heat conductive or non-stick material.

In FIGS. 8A and 8B, the spiral-mandrel 32a with the stent 10 positioned thereon is shown mounted on a stent manufacturing device 38. The stent manufacturing device 38 can include a motor 38a for rotating the stent, a motor 38b for moving the stent longitudinally and a support members 38c and 38d for mounting the spiral-mandrel 32a (or alternative embodiments) thereon. Thus, in one embodiment of the method of the present invention, the wire 30 may be coiled around the mandrel 28 forming a spiral-mandrel 32 (explained above). The mandrel 28 may or may not be removed thereafter. If the mandrel 28 is not removed, the wire 30 acts as a "spacer" to place a gap between the surface of the mandrel 28 and the stent 10 for the purpose of polishing. Subsequently, the stent 10 may be positioned onto the spiral-mandrel 32 forming a "stent spiral-mandrel assembly". The stent spiral-mandrel assembly may then be mounted onto the device 38 for polishing. The stent 10 may thereafter be subjected to intense heat (indicated by arrows 42) via convection or radiation, or "heat flashing," from a heat source 40 in order to round out the sharp corners 22 of the stent struts 12 and the connecting elements 14 thereof. The heat source can be at a distance 0.25" to 2.0" from the spiral-mandrel assembly, preferably 0.5". The duration of the heat flashing can be between two and eight or ten seconds, preferably approximately five seconds. The duration depends on factors such as the material of the stent 10, the distance of the stent 10 to the heat source 40 and the temperature used. The temperature of the heat can be from about 40° C. to about 175° C., preferably about 55° C. to about 65° C.

In some embodiments, the stent 10 can be rotated (arrow 38e) during the heating process so as to ensure even application of heat. For example, the stent can be rotated about 10 to about 3500 rpm, preferably about 100 rpm to about 1000 rpm. In other embodiments, an area of the stent 10 can be heated, following by termination of the heat, followed by a degree of rotation of the stent 10. Subsequently, the heat can be applied again to a new segment of the stent and this process can be repeated. In other embodiments, the stent 10 can be moved longitudinally (arrow 38f) while the heat is being applied. Yet, in other embodiments, the stent 10 can be heated, followed by termination of the heat, followed by moving the stent 10 longitudinally to expose a different area of the stent to the heat treatment. It should be understood that any combination of the movements described above can be used for heat polishing the stent 10 of the present invention.

The external heat source 40 may be from a heater coil, an Nd-YAG laser, a radio frequency ("RF") heater or an apparatus for blowing hot air or gas (e.g., inert gas), for example. Moreover, the heat generated from the heat source 40 can be in a range between the glass transition temperature ("Tg") and melting temperature ("Tm") of a polymer. In some embodiments the heat generated can be equal to or greater than the Tg of a polymer of the stent 10 and less than the Tm of a polymer of the stent 10. In some embodiments, the temperature can be equal to or above Tm. In some embodiments, the duration of exposure of such temperatures is of sufficient time and under conditions so as to allow a temperature of the polymer of the stent, mostly around the edges of the strut, to reach a temperature equal to or above Tg of the polymer. In some embodiments, it is preferable that the temperature of the polymer of the stent reach a temperature equal to or greater than the Tg of the polymer but not greater than the Tm of the polymer. Should the stent be composed of multiple polymers, such temperature refers to the temperature of at least one of the polymers that achieves the desired polishing of the stent. In this manner, the sharp corners 22 on both the abluminal surface and the luminal surface of the stent 10 may be rounded out.

More particularly, the spiral-mandrel 32a allows heat from the external heat source 40 to reach the luminal surface of the stent 10 due to its hollow nature and the spacing between the coils (see FIG. 9A). That is, heat from the external heat source 40 will pass through the interstitial gaps 16 of the stent and through the spacing of the coils of the spiral-mandrel 32a, ultimately reaching the lumen 44 (shown in FIG. 4C) of the spiral-mandrel 32a. As such, the heat inside the lumen 44 will circulate and contact the luminal surface of the stent 10, including at least one sharp corner 22, resulting in the polishing thereof.

Alternatively, in the embodiment in which the spiral-mandrel 32 is formed from a heat conductive material, the heat transferred to the spiral-mandrel 32 from the heat source 40 may in turn be transferred to the luminal surface of the stent 10, including at least one sharp corner 22, resulting in the polishing thereof. In this manner, both the luminal surface and the abluminal surface of the stent may be polished simultaneously.

In the alternative embodiment in which the mandrel 28 is not removed, the coils of the spiral-mandrel 32a will act as a "spacer" between the mandrel 28 and the stent 10, as illustrated in FIG. 9B. Thus, heat from the heat source 40 will pass through the interstitial gaps 16 of the stent and through the spacing of the coils of the spiral-mandrel 32a, thereby accessing the luminal surface of the stent 10 resulting in the polishing thereof.

Figure 10A:
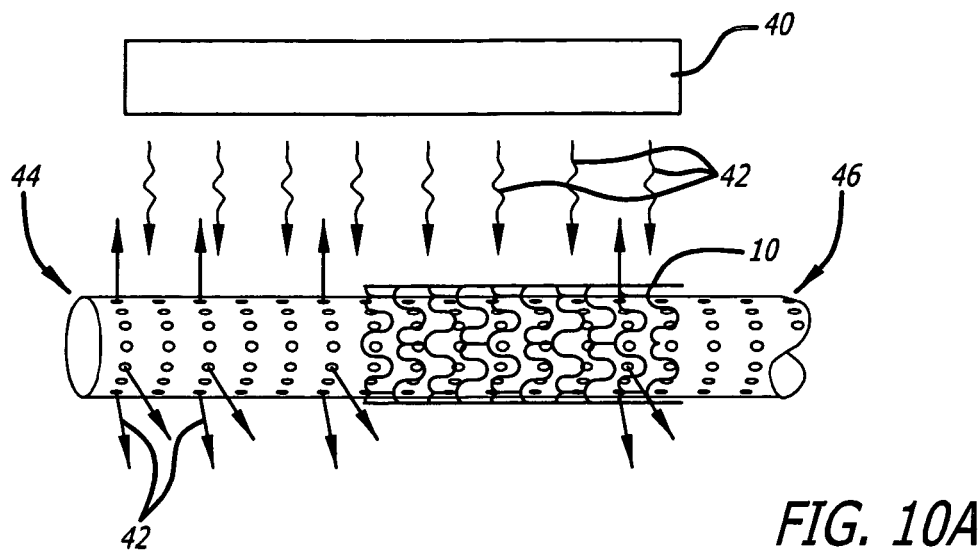
FIG. 10A illustrates a method of the present invention in which a stent is mounted on a hypotube for heat polishing of the stent.

FIG. 10A illustrates another embodiment of the method of the present invention, which method uses a conduit, such as a porous hypotube 46, to polish the stent 10. The porous hypotube 46 can have two open ends, as illustrated by FIG. 10A and a lumen 44 extending therethrough. In one embodiment, the hypotube 46 can have one open end and one closed end with the lumen 44 terminating at the closed end. Alternatively, the hypotube 46 can have both opposing ends closed, such that the lumen 44 defines a hollow bore within the support structure. Such closed end(s) is mounted on a polishing system, such as the apparatus illustrated in FIG. 10B. The pores can be interconnected or discrete, and can extend through the body of the structure so as to allow for heat to exit out from the pores. The hypotube 46 may be heat conductive or non-conductive, and can be stainless steel, aluminum, gold or any combination thereof, for example. Moreover, the hypotube 46 may be formed from or coated with a substance, such as parylene or Teflon, to prevent the stent 10 from adhering to the hypotube 46 during the polishing process. In this method, the heat source 40 may be internal to the hypotube 46, such as, for example, a (very) small heater coil or coils, or a heating pin capable of being inserted therein. The heat (shown by arrows 42) may therefore heat the stent 10 from within. Alternatively, the heat source 40 may be external to the hypotube 46, with the heat (shown by arrows 42) being transferred through a lumen 44 and pores of the hypotube 46. In some embodiments, the heat source can be generated from a heat source which heats a gas which is subsequently blown through the lumen 44 and out through the pores of the hypotube 46. The gas can be, for example, air or an inert gas. Once a stent 10 is mounted on the hypotube 46, the luminal surface of the stent will be exposed to heat from the heat source 40 either externally or internally as described above. In this manner, the luminal surface of the stent 10 is polished. It should be noted that for all embodiments described herein, the heat source can be internal, i.e., in the lumen 44 of the spiral-mandrel 32a, or any alternative embodiments 32b, 32c, 35, 35b, 46 or 48, or external. Certainly, in some embodiments, it can be both.

Figure 10B:
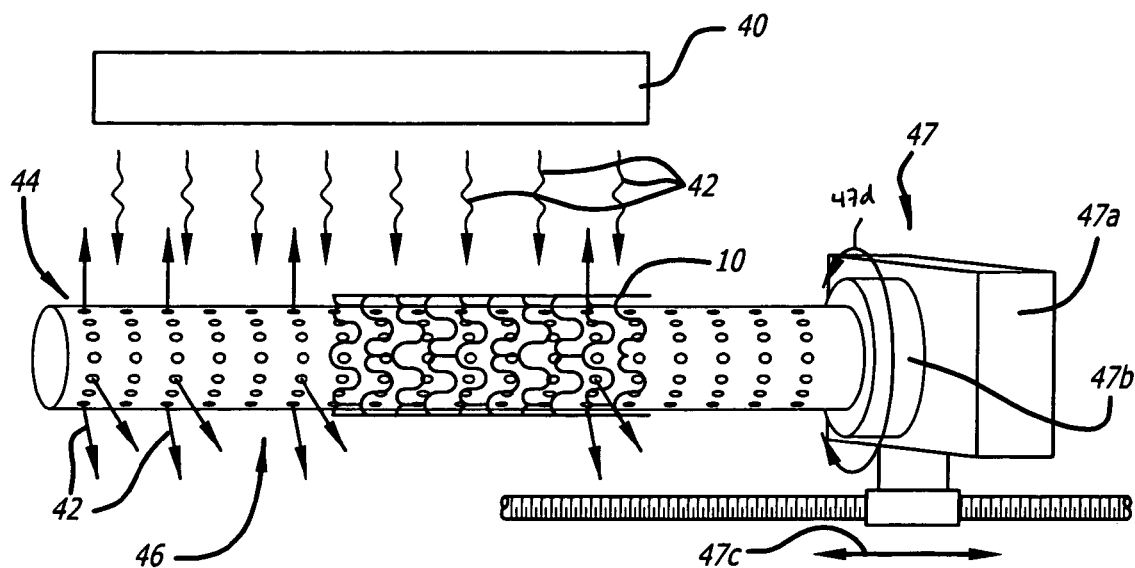
FIG. 10B illustrates a method (and assembly) of the present invention in which a stent is moved rotationally and/or axially relative to a heat source for heat polishing of the stent.

A further alternative assembly is depicted in FIG. 10B generally at 47. In this assembly, the hypotube 46, which supports the stent, can be mounted on a spinning mechanism 47a which spins the stent 10 relative to a fixed heating source 40. The mandrel can be mounted in a chuck 47b that accommodates different diameters. The chuck 47b in turn, can be connected to a motorized mechanism wherein the rotational speed can thereby be controlled. One option is to couple it to a computer control, which allows for controlled axial movement 47c into the heat source and controlled rotation thereof. In some embodiments, the stent 10 can be rotated (arrow 47d) during the heating process so as to ensure even application of heat. For example, the stent can be rotated about 10 rpm to about 3500 rpm, preferably about 100 rpm to about 1000 rpm. In other embodiments, an area of the stent 10 can be heated, following by termination of the heat, followed by a degree of rotation of the stent 10. Subsequently, the heat can be applied again to a new segment of the stent and this process can be repeated. In other embodiments, the stent 10 can be moved axially (arrow 47c) while the heat- is being applied. Yet, in other embodiments, the stent 10 can be heated, followed by termination of the heat, followed by moving the stent 10 axially to expose a different area of the stent to the heat treatment. It should be understood that any combination of the movements described above can be used for heat polishing the stent 10 of the present invention.

Figure 11:
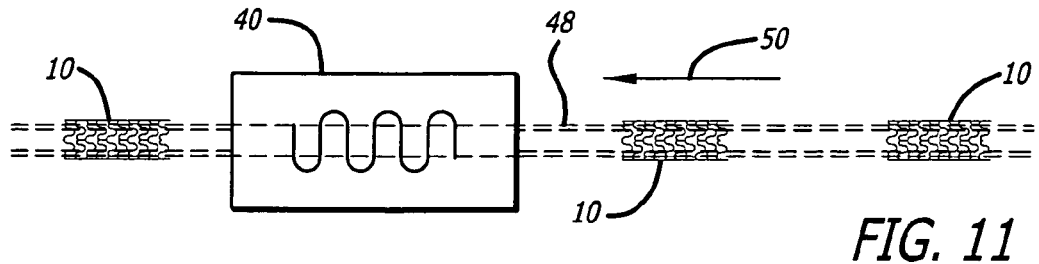
FIG. 11 illustrates another method of the present invention in which a stent is mounted on a conveyor for polishing of the stent at a heating station.

FIG. 11 illustrates another alternative embodiment of the method of the present invention. In this figure, a "conveyor mechanism" 48 is illustrated with a plurality of stents 10 mounted thereon, in spaced relation. In one embodiment, the conveyor mechanism 48 may be a form of the spiral-mandrel 32a, though considerably longer, or a series of mandrels connected in a spaced fashion relative to one another. The conveyor mechanism 48, with a plurality of stents 10 mounted thereon, may be mechanically moved (depicted by arrow 50) towards a heat source 40 for polishing of the stents. In an alternative embodiment, the conveyor mechanism 48 may be configured to suspend the stent 10 at both ends thereof in the air as the stents move toward (and away from) the heat source 40. It should be understood that the conveyor mechanism 48 may be configured in a multitude of forms, with a principle goal that the conveyor mechanism 48 allows heat to pass through for the polishing of the luminal (and abluminal) surface(s) of the stent 10, in a consistent and efficient manner. Further, the heat source 40 can define a heat polishing chamber through which the stent 10 passes by the conveyor mechanism 48. The stent may move at a continuous speed through the chamber, or at a slowed speed or even briefly stop for the heat polishing step.

Figure 12A:
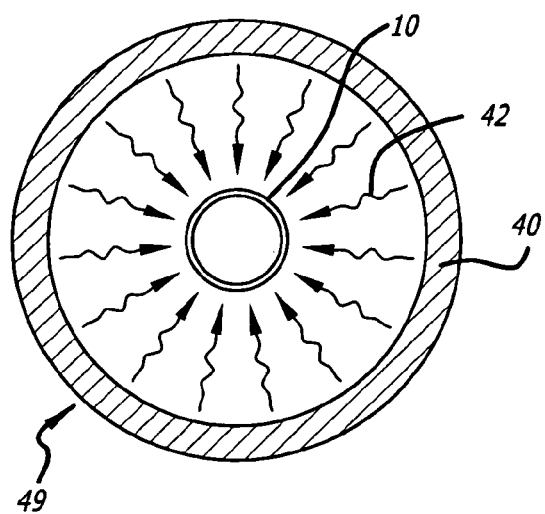
FIG. 12A is a cross-sectional view of a further method of the present invention in which a stent is mounted on a mandrel (or one of the alternative embodiments herein) for heat polishing thereof.
Figure 12B:
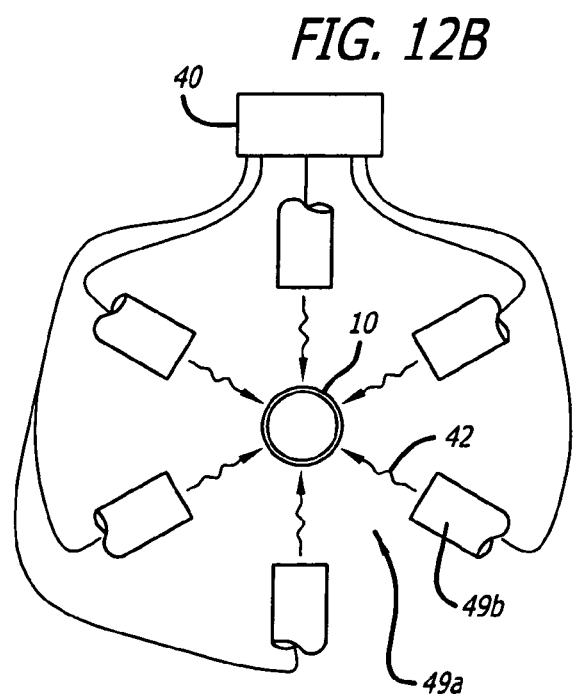
FIG. 12B is a view similar to FIG. 12A of a variation thereof.

FIG. 12A shows generally at 49 an alternative system for heat polishing a stent 10 which can, for example, be mounted on a spiral-mandrel, as discussed above. The heat 42 from a heat source 40, such as a heater coil, is applied to the stent radially via radiation or convection. A variation of system 49 is shown by system 49a in FIG. 12B. It shows that the heat 42 from a heat source 40 can be forcibly applied through tubes 49b directed radially towards the stent 10. Tubes 49b can be positioned at equal distances around the stent 10 so that the application of heat 42 is evenly distributed. In some embodiments, the heat distribution is even across the length of the stent 10. An even distribution of heat can be important for all embodiments for uniformity in polishing. Rotation and axial movement of the stent 10 during the polishing process may certainly contribute to such uniform heat distribution. In some embodiments, selective application of heat may be required as some regions of the stent 10 may require more polishing than others. Accordingly, local and concentrated application of heat would be more beneficial as opposed to heat treatment of the whole stent at once.

Figure 13:
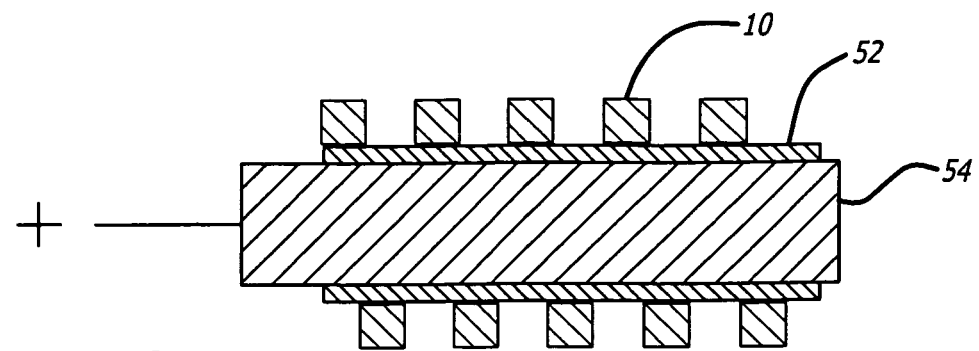
FIG. 13 illustrates a still further alternative embodiment of a method of the present invention in which a stent is mounted on a heat conducting sleeve or tube for heat polishing of the stent.

FIG. 13 illustrates yet another alternative embodiment of the method of the present invention. In this figure, a stent 10 is shown mounted on a heat conducting tube 52. In some embodiments, the heat conducting tube 52 can be in intimate contact with the luminal surface of the stent 10. A heating element 54 may be located inside the lumen of the heat conducting tube 52. In some embodiments, the heating element 54 may be a heater rod which is, for example, electrically energized. In some embodiments, the heating element 54 can be in intimate contact with the heat conducting tube 52, as well. When heat is applied to the heating element 54, the heat is transferred to the heat conducting tube 52, which in turn is transferred to the luminal surface of the stent 10. The luminal surface of the stent 10 is thereby polished, rounding out the "sharp corners" 22 of the stent 10 thereof. The construction and operation of the heating element 54 and tube 52 can take many forms as would be apparent to those skilled in the art.

Figure 14:
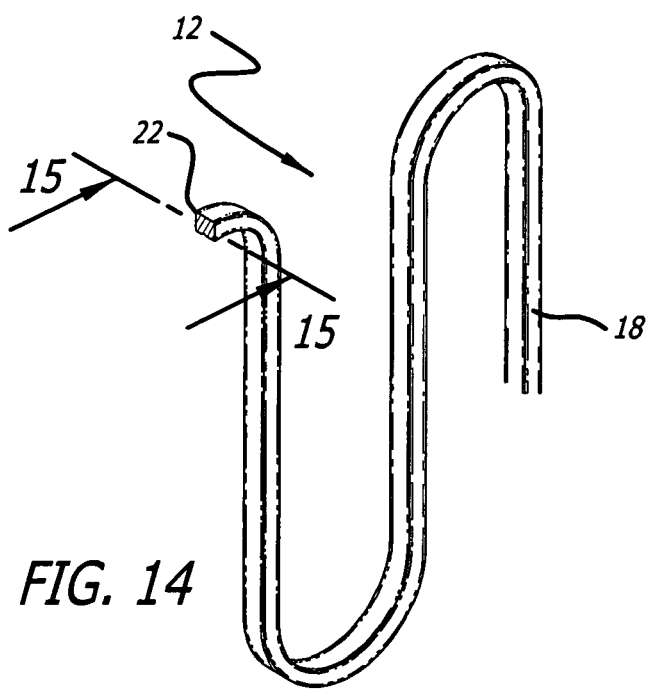
FIG. 14 shows an enlarged portion of a strut of a stent after having been polished in accordance with any of the embodiments of the present invention.
Figure 15:
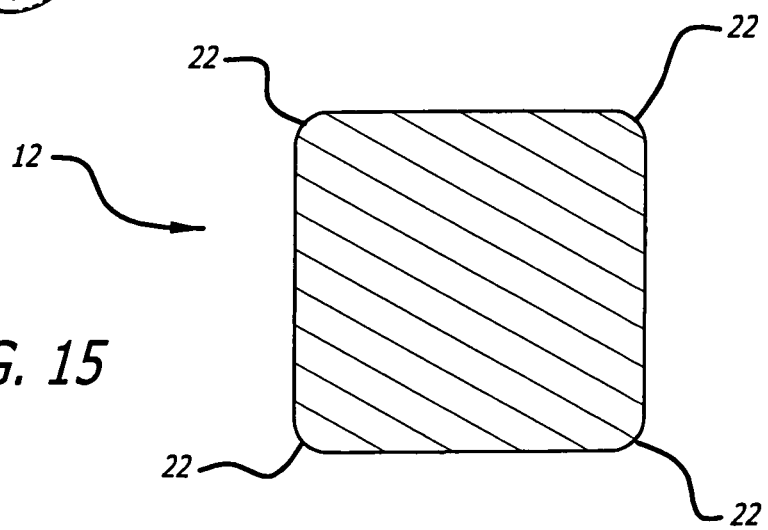
FIG. 15 shows an enlarged cross-sectional view of the strut of FIG. 14 taken on line 15-15 thereof.

An enlarged portion of a strut 12 of a stent 10 resulting from an embodiment of a method of the present invention is illustrated in FIG. 14. After polishing, the strut 12 may still have a cross-section with a "square" shape with four surfaces, walls or sides 18 and four corners 22; however, the corners 22 may be "rounded out", i.e., changed from an angular to a non-angular configuration, due to heat treatment or flashing from the heat source 40 (see FIG. 15). In FIG. 15, a cross-section of strut 12 taken at line 15-15 of FIG. 14 illustrates these features in greater detail. The polished strut 12 includes four surfaces, walls or sides 18 and four rounded corners 22. Because the corners 22 are rounded, the strut 12 is not as susceptible and may even be immune to cracks initiated by stress risers. Moreover, heat treatment or flashing from the heat source 40 will only affect the surface morphometry of the stent 12, thus maintaining the integrity of the stent for subsequent use.

Figure 16:
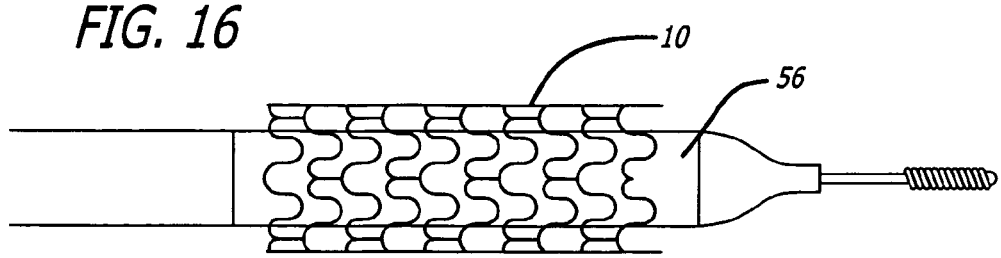
FIG. 16 illustrates a stent polished pursuant to a method of the present invention on a catheter and in an expanded state.
Figure 17:
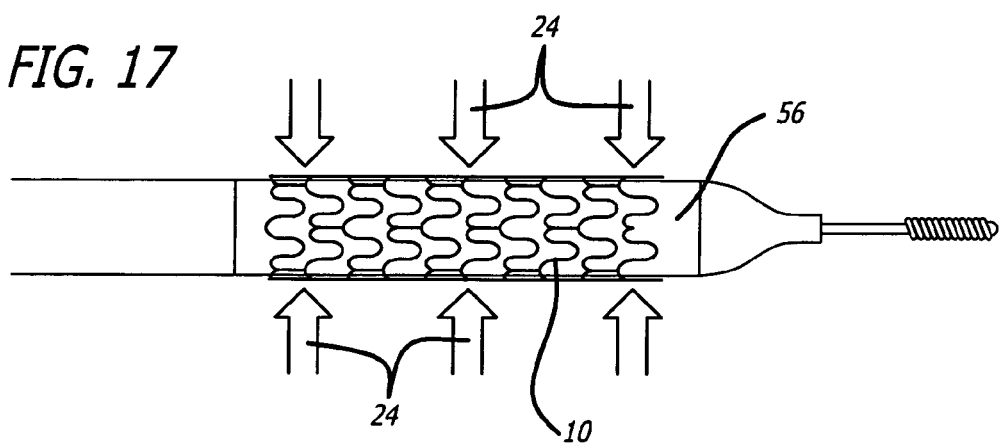
FIG. 17 illustrates the stent of FIG. 16 in a crimped state on the catheter of that figure.

As discussed before, crimping or expansion of the stent 10 subjects the struts 12 and connecting elements 14 to stress, which may in turn cause the stent to crack. Together, FIGS. 16 and 17 represent an illustrative example of a crimping process as known in the prior art but used on a stent polished according to the present invention. In FIG. 16, a stent 10 is shown on a catheter 56 in an expanded state. By applying pressure to the outer diameter of the stent (shown by arrows 24), the stent 10 is secured to the catheter 56, or "crimped" thereon, and thereafter ready for delivery into a bodily lumen. A stent is typically manufactured in an expanded state and may be crimped onto a catheter by a manufacturer, or, alternatively, may be left in an expanded state to be subsequently crimped onto a catheter by a user.

Figure 18:
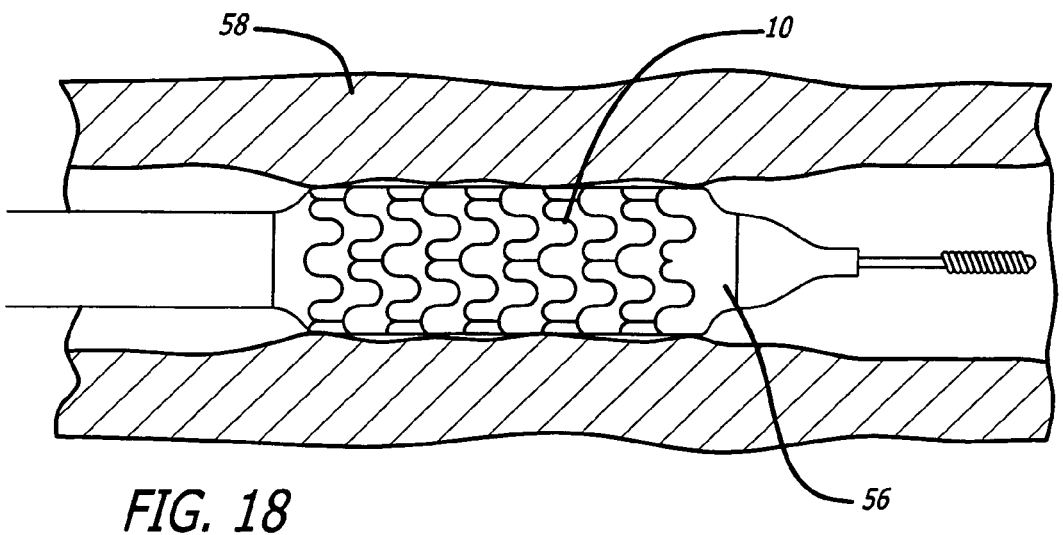
FIG. 18 illustrates the stent of FIG. 17 in an expanded state in a bodily lumen.

In FIG. 18, the stent 10 is shown in an expanded state during delivery to a bodily lumen 58 using a balloon-expandable stent assembly. It should be understood that alternative stent assemblies, such as a self-expanding stent assembly, will subject the stent 10 to expansion as illustrated in this figure, within the bodily lumen. Thus, the present invention for polishing the entire surface of a stent, including the abluminal and luminal surfaces of the stent, substantially or completely reduces or eliminates cracks caused by the crimping and expansion processes.

From the foregoing detailed description, it will be evident that there are a number of changes, adaptations and modifications of the present invention which come within the province of those skilled in the art. The scope of the invention includes any combination of the elements from the different species or embodiments disclosed herein, as well as subassemblies, assemblies, and methods thereof. For example, instead of a polymeric stent a non-polymeric stent or other type of device (including other types of implantable medical devices) can be used. Further, the stent or other device may be polished using solvents instead of heat. The invention can further be used for application of an active agent or drug. The active agent or drug can be embedded or compounded in the body of the stent or disposed on the body as a coating. The coating can include a polymer carrier and preferably should be deposited after the polishing process. It is intended that all such variations not departing from the spirit of the invention be considered as within the scope thereof.

What is claimed is:

1. A method of polishing a polymeric stent, comprising:
   mounting an unpolished polymeric stent on a mandrel; and
   directing heat into an interior space of the unpolished polymeric stent and against a luminal surface of the stent to thereby polish the luminal surface, wherein the unpolished polymeric stent is mounted on the mandrel before the directing; and wherein the mandrel is a tube having wall openings, and the directing includes directing the heat into the tube and out through the openings and against the luminal surface.

2. The method of claim 1, wherein the heat is radiation heat.

3. The method of claim 1, wherein the heat is convection heat.

4. The method of claim 1, wherein the heat is hot gas.

5. The method of claim 1, wherein the directing includes directing the heat axially into the interior space of the stent.

6. A method of polishing a polymeric stent, comprising:
mounting an unpolished polymeric stent on a mandrel; and
directing heat into an interior space of the unpolished polymeric stent and against a luminal surface of the stent to thereby polish the luminal surface, wherein the unpolished polymeric stent is mounted on the mandrel before the directing; and
wherein the mandrel includes interconnected spaced rings and openings defined between the rings, the mounting includes mounting the unpolished stent on the rings, and the directing includes directing the heat into the mandrel and out through the openings and against the luminal surface.

7. The method of claim 1, wherein the temperature of a polymer of the stent is increased to equal to or greater than a glass transition temperature and less than a melting temperature of the polymer.

8. The method of claim 1, wherein the temperature of a polymer of the stent is increased to equal to or less than a melting temperature of the polymer.

9. The method of claim 1, wherein the heat is at a temperature equal to or greater than a glass transition temperature of a polymer of the stent.

10. The method of claim 1, wherein the heat is at a temperature equal to or greater a melting temperature of a polymer of the stent.

11. The method of claim 1, wherein the heat is from a heater coil, radio frequency heater or gas blower.

12. The method of claim 1, wherein the heat is from an element capable of being inserted into a hollow longitudinal bore of the stent.

13. The method of claim 1, wherein the directing includes the luminal surface being subjected to the heat for 3 to 8 seconds at a selected temperature of about 40° C. to about 175° C.

14. The method of claim 1, wherein the heat polishes an abluminal surface of the stent.

15. The method of claim 1, wherein the directing is at a heating station, and further comprises conveying the unpolished stent by the station.

16. The method of claim 15, wherein the conveying includes the stent being stopped during the directing at the heating station.

17. A method of polishing a polymeric stent, comprising:
mounting a polymeric stent on a cylindrical braided device, and
directing heat into an interior space and against a luminal surface of the polymeric stent to thereby polish the luminal surface, wherein the directing includes directing the heat through gaps of the wall of the braided device.

18. The method of claim 1, additionally including rotating the stent during the application of heat.

19. The method of claim 18, additionally including rotating the stent during the polishing process, wherein the application of heat is terminated before the rotation of the stent and wherein the rotation of the stent is terminated prior to application of the heat.

20. A method of polishing a polymeric stent, comprising:
mounting a stent made from a material including a polymer onto a structure having a series of gaps; and
after the mounting, subjecting the stent to heat from a heat source so as to modify a surface morphometry of at least a section of the stent from an angular configuration to a non-angular configuration;
wherein the heat source is positioned internal to the structure.

21. The method of claim 20, wherein the structure includes a tubular coiled wire, a tubular braided structure, a porous sheath, a porous hypotube or a series of interconnecting cylindrical rings.

22. The method of claim 20, wherein the structure is made from a material including a heat conductive material.

23. The method of claim 20, wherein the structure comprises a metallic material.

24. The method of claim 20, wherein the structure is made from a non-heat conductive material.

25. The method of claim 20, wherein the heat is at a temperature equal to or greater than a glass transition temperature of the polymer.

26. The method of claim 20, wherein the heat is at a temperature equal to or greater than a melting temperature of the polymer.

27. The method of claim 20, wherein the temperature of the polymer is increased to greater than or equal to a glass transition temperature of the polymer.

28. The method of claim 20, wherein the temperature of the polymer is increased to less than or equal to a melting temperature of the polymer.

29. A method of polishing a luminal surface of a polymeric stent, comprising:
mounting an unpolished polymeric stent on and around a cylindrical surface and in direct thermal contact therewith; and
heating the cylindrical surface to thereby heat and polish the luminal surface of the stent mounted thereon;
wherein the cylindrical surface is a heat conducting tube which is mounted on a heating element, and the heating includes heating the heating element to thereby heat the heat conducting tube, which in turn heat polishes the luminal surface.

* * * * *

UNITED STATES PATENT AND TRADEMARK OFFICE
CERTIFICATE OF CORRECTION

PATENT NO.       : 7,658,880 B2                                               Page 1 of 1
APPLICATION NO.  : 11/194089
DATED            : February 9, 2010
INVENTOR(S)      : Patrick P. Wu It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1226 days.

Signed and Sealed this

Twenty-eighth Day of December, 2010

David J. Kappos
*Director of the United States Patent and Trademark Office*